United States Patent
Chiou et al.

(10) Patent No.: US 10,336,801 B2
(45) Date of Patent: Jul. 2, 2019

(54) CHEMOKINE-CYTOKINE FUSION PROTEINS OF SDF-1 AND CD40L

(71) Applicant: NATIONAL CHUNG HSING UNIVERSITY, Taichung (TW)

(72) Inventors: Shiow-Her Chiou, Taichung (TW); Kuan-Chih Chow, Taichung (TW); Jui-Hung Shien, Taichung (TW); Yi-Hsin Fan, Taichung (TW); Pei-Hua Lin, Taichung (TW); Pei-Shan Wu, Taichung (TW)

(73) Assignee: NATIONAL CHUNG HSING UNIVERSITY, Taichung (TW)

(*) Notice: Subject to any disclaimer, the term of this patent is extended or adjusted under 35 U.S.C. 154(b) by 0 days.

(21) Appl. No.: 15/658,929

(22) Filed: Jul. 25, 2017

(65) Prior Publication Data

US 2017/0327554 A1 Nov. 16, 2017

Related U.S. Application Data

(63) Continuation of application No. 14/649,714, filed as application No. PCT/CN2012/001629 on Dec. 5, 2012, now abandoned.

(51) Int. Cl.
| | |
|---|---|
| C07K 19/00 | (2006.01) |
| C07K 14/55 | (2006.01) |
| C07K 14/525 | (2006.01) |
| A61K 39/39 | (2006.01) |
| C07K 14/52 | (2006.01) |
| C07K 14/705 | (2006.01) |
| C07K 14/54 | (2006.01) |
| A61K 39/00 | (2006.01) |

(52) U.S. Cl.
CPC .............. *C07K 14/55* (2013.01); *A61K 39/39* (2013.01); *C07K 14/52* (2013.01); *C07K 14/521* (2013.01); *C07K 14/522* (2013.01); *C07K 14/525* (2013.01); *C07K 14/5421* (2013.01); *C07K 14/70575* (2013.01); *A61K 2039/55533* (2013.01); *C07K 2319/00* (2013.01)

(58) Field of Classification Search
None
See application file for complete search history.

(56) References Cited

U.S. PATENT DOCUMENTS

| 2002/0150553 A1 | 10/2002 | Martins-Green |
| 2005/0053579 A1 | 3/2005 | Galipeau et al. |

OTHER PUBLICATIONS

Altenburg et al. The Potent Anti-HIV Activity of CXCL12g Correlates with Efficient CXCR4 Binding and Internalization. J Virol. Aug. 2007;81(15):8140-8.*
Cotter et al. Regulation of Human Immunodeficiency Virus Type 1 Infection, b-Chemokine Production, and CCR5 Expression in CD40L-Stimulated Macrophages: Immune Control of Viral Entry. J Virol. May 2001;75(9):4308-20.*
Arai et al., "Design of the Linkers which Effectively Separate Domains of a Bifunctional Fusion Protein", Protein Engineering, vol. 14, No. 8 (2001) pp. 529-532.
Nomura et al., "Enhancement of Anti-tumor Immunity by Tumor Cells Transfected with the Secondary Lymphoid Tissue Chemokine EBI-1-Ligand Chemokine and Stromal Cell-Derived Factor-1α Chemokine Genes", Int. J. Cancer, vol. 91 (2001) pp. 597-606.
Robbins et al., "Interleukin-2-Induced Chemotaxis of Human T-lymphocytes", J Lab Clin Med, vol. 106, No. 4, (1986) pp. 340-345.
Stebler et al., "Primordial Germ Cell Migration in the Chick and Mouse Embryo: the Role of the Chemokine SDF-1/CXCL12", Developmental Biology, vol. 272 (2004) pp. 351-361.
Tsai et al., UniProtKB—Q5UB38 (Q5UB38_CHICK) UniProt; Dec. 7, 2004.
Wilkinson et al., "Chemoattractant Activity of IL-2 for Human Lymphocytes: A Requirement for IL-2 Receptor β-Chain", Immunology, vol. 82 (1994) pp. 134-139.

* cited by examiner

*Primary Examiner* — Dong Jiang
(74) *Attorney, Agent, or Firm* — Birch, Stewart, Kolasch & Birch, LLP

(57) ABSTRACT

The present invention provides a fusion protein, comprising a chemokine polypeptide, which is a chemokine or a receptor binding domain thereof; and a cytokine polypeptide connected to said chemokine polypeptide, which is an interleukin, a TNF-superfamily cytokine or a receptor-binding domain thereof; wherein the chemokine polypeptide and the cytokine polypeptide have a common target cell, and the fusion protein has an improved chemokine activity as compared to the chemokine polypeptide, and an improved cytokine activity as compared to the cytokine polypeptide.

3 Claims, 9 Drawing Sheets

Specification includes a Sequence Listing.

SEQUENCE LISTING

```
<160> NUMBER OF SEQ ID NOS: 48

<210> SEQ ID NO 1
<211> LENGTH: 263
<212> TYPE: DNA
<213> ORGANISM: Gallus gallus

<400> SEQUENCE: 1
ctctgtcgca aggtaggacg ctggtaaaga tggggaatga gctgcggtgc cagtgcatta      60
gcactcattc taagttcatc caccctaaat ccattcaaga tgtgaagctg acgccaagcg     120 gccccactg caagaatgtt gaaatcatag ctactctaaa ggatggaaga gaggtgtgct     180 tggacccac tgctccctgg gtacagctga tcgtaaaggc acttatggcc aaggctcagc     240
tcaattctga tgcaccactg tga                                             263

<210> SEQ ID NO 2
<211> LENGTH: 87
<212> TYPE: PRT
<213> ORGANISM: Gallus gallus
```

<400> SEQUENCE: 2

Ala Leu Ser Gln Gly Arg Thr Leu Val Lys Met Gly Asn Glu Leu Arg
1               5                   10                  15

Cys Gln Cys Ile Ser Thr His Ser Lys Phe Ile His Pro Lys Ser Ile
                20                  25                  30

Gln Asp Val Lys Leu Thr Pro Ser Gly Pro His Cys Lys Asn Val Glu
            35                  40                  45

Ile Ile Ala Thr Leu Lys Asp Gly Arg Glu Val Cys Leu Asp Pro Thr
        50                  55                  60

Ala Pro Trp Val Gln Leu Ile Val Lys Ala Leu Met Ala Lys Ala Gln
65                  70                  75                  80

Leu Asn Ser Asp Ala Pro Leu
                85

<210> SEQ ID NO 3
<211> LENGTH: 237
<212> TYPE: DNA
<213> ORGANISM: Sus scrofa

<400> SEQUENCE: 3
gcaagagtaa gtgcagaact tcgatgccag tgcataaata cgcattccac acctttccac    60
cccaaattta tcaaggaact gagagtgatt gagagtggac cccactgtga aaattcagaa   120
atcattgtta agcttgtcaa tggaaaagag gtctgcctgg accccaagga aaagtgggtg   180
cagaaggttg tacagatatt tttgaagaga actgagaagc aacaacaaca gcagtaa      237

<210> SEQ ID NO 4
<211> LENGTH: 78
<212> TYPE: PRT
<213> ORGANISM: Sus scrofa

<400> SEQUENCE: 4

Ala Arg Val Ser Ala Glu Leu Arg Cys Gln Cys Ile Asn Thr His Ser
1               5                   10                  15

Thr Pro Phe His Pro Lys Phe Ile Lys Glu Leu Arg Val Ile Glu Ser
                20                  25                  30

Gly Pro His Cys Glu Asn Ser Glu Ile Ile Val Lys Leu Val Asn Gly
            35                  40                  45

Lys Glu Val Cys Leu Asp Pro Lys Glu Lys Trp Val Gln Lys Val Val
        50                  55                  60

Gln Ile Phe Leu Lys Arg Thr Glu Lys Gln Gln Gln Gln
65                  70                  75

<210> SEQ ID NO 5
<211> LENGTH: 240
<212> TYPE: DNA
<213> ORGANISM: Bos taurus

<400> SEQUENCE: 5
gcagttctgt caagaatgag tacagaactt cgatgccaat gcataaaaac acattccaca    60
cctttccacc ccaaatttat caagaattg agagttattg agagtgggcc acactgtgaa   120
aattcagaaa tcattgttaa gcttaccaat ggaaacgagg tctgcctaaa ccccaaggaa   180
aagtgggtgc agaaggttgt gcaggtattt gtgaagagag ctgagaagca agatccatga   240

-continued

<210> SEQ ID NO 6
<211> LENGTH: 79
<212> TYPE: PRT
<213> ORGANISM: Bos taurus

<400> SEQUENCE: 6

Ala Val Leu Ser Arg Met Ser Thr Glu Leu Arg Cys Gln Cys Ile Lys
1               5                   10                  15

Thr His Ser Thr Pro Phe His Pro Lys Phe Ile Lys Glu Leu Arg Val
            20                  25                  30

Ile Glu Ser Gly Pro His Cys Glu Asn Ser Glu Ile Ile Val Lys Leu
        35                  40                  45

Thr Asn Gly Asn Glu Val Cys Leu Asn Pro Lys Glu Lys Trp Val Gln
    50                  55                  60

Lys Val Val Gln Val Phe Val Lys Arg Ala Glu Lys Gln Asp Pro
65                  70                  75

<210> SEQ ID NO 7
<211> LENGTH: 234
<212> TYPE: DNA
<213> ORGANISM: Homo sapiens

<400> SEQUENCE: 7
gcagttttgc caaggagtgc taaagaactt agatgtcagt gcataaagac atactccaaa      60
cctttccacc ccaaatttat caagaactg agagtgattg agagtggacc acactgcgcc     120
aacacagaaa ttattgtaaa gctttctgat ggaagagagc tctgtctgga ccccaaggaa    180
aactgggtgc agagggttgt ggagaagttt ttgaagaggg ctgagaattc ataa          234

<210> SEQ ID NO 8
<211> LENGTH: 77
<212> TYPE: PRT
<213> ORGANISM: Homo sapiens

<400> SEQUENCE: 8

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser
65                  70                  75

<210> SEQ ID NO 9
<211> LENGTH: 270
<212> TYPE: DNA
<213> ORGANISM: Gallus gallus

<400> SEQUENCE: 9
atggacctcc gcgccctggc tctgctcgcc tttgccctgg cagtcatctc cctgtcggag      60
gagaagcctg tcagcctgac ttaccgatgc ccctgtcgat tcttcgagag caacgtggcg     120
agggccaaca ttaagcacct caaaatcctt ccactccca actgctcgct tcagattgtt     180
gcaaggctca agagcaacag caagcaagtg tgcattgatc ccaagctaaa atggatccag     240
gaatatctgg agaaagcttt aaacaagtaa                                       270

<210> SEQ ID NO 10
<211> LENGTH: 89
<212> TYPE: PRT
<213> ORGANISM: Gallus gallus

<400> SEQUENCE: 10

Met Asp Leu Arg Ala Leu Ala Leu Leu Ala Phe Ala Leu Ala Val Ile
1               5                   10                  15

Ser Leu Ser Glu Glu Lys Pro Val Ser Leu Thr Tyr Arg Cys Pro Cys
            20                  25                  30

Arg Phe Phe Glu Ser Asn Val Ala Arg Ala Asn Ile Lys His Leu Lys
        35                  40                  45

Ile Leu Ser Thr Pro Asn Cys Ser Leu Gln Ile Val Ala Arg Leu Lys
50                  55                  60

Ser Asn Ser Lys Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 11
<211> LENGTH: 351
<212> TYPE: DNA
<213> ORGANISM: Sus scrofa

<400> SEQUENCE: 11
atgggtgtca aggtcctcgc cgtgctggcc ctcgtgctga ccgcgctctg cctcagcgat      60
gagaaaccgg tcagcctgag ctacagatgc ccttgccgat tctttgagag ccacgttgcc     120
agagccaaca tcaagcatct caagatcctc aacactccga actgtgccct tcagatcgtg     180
gcacggctga gagcaacaa tagacaagtg tgcattgacc caaaattgaa gtggattcag      240
gaatacctgg agaaagcttt aaacaaaccc agtcccactc tctcgggcct gacctctgcc     300
ctgggaagca gcctggccag cactactgtc ggcatcacca gcaggagctg a              351

<210> SEQ ID NO 12
<211> LENGTH: 116
<212> TYPE: PRT
<213> ORGANISM: Sus scrofa

<400> SEQUENCE: 12

Met Gly Val Lys Val Leu Ala Val Leu Ala Leu Val Leu Thr Ala Leu
1               5                   10                  15

Cys Leu Ser Asp Glu Lys Pro Val Ser Leu Ser Tyr Arg Cys Pro Cys
            20                  25                  30

Arg Phe Phe Glu Ser His Val Ala Arg Ala Asn Ile Lys His Leu Lys
        35                  40                  45

Ile Leu Asn Thr Pro Asn Cys Ala Leu Gln Ile Val Ala Arg Leu Lys
50                  55                  60

Ser Asn Asn Arg Gln Val Cys Ile Asp Pro Lys Leu Lys Trp Ile Gln
65                  70                  75                  80

Glu Tyr Leu Glu Lys Ala Leu Asn Lys Pro Ser Pro Thr Leu Ser Gly
                85                  90                  95

Leu Thr Ser Ala Leu Gly Ser Ser Leu Ala Ser Thr Thr Val Gly Ile
                100                 105                 110

Thr Ser Arg Ser
            115

<210> SEQ ID NO 13
<211> LENGTH: 270
<212> TYPE: DNA
<213> ORGANISM: Bos taurus

<400> SEQUENCE: 13

```
atggatgcca aggtcttcgt cgtgctggcc ctcgtgctga ctgcgctgtg cctcagcgac      60
gcgaaaccgg tcagcctgag ctacagatgc ccttgccgat tctttgagag ccatgtcgcc     120
aaagccaacg tcaagcacct caaaatcctc aacactccaa actgctccct tcagatcgtg     180
gcaaggctga gaacaacaa taggcaagtg tgcattgacc cgaaattgaa gtggattcag      240
gaatacctgg acaaagcttt aaacaagtaa                                      270
```

<210> SEQ ID NO 14
<211> LENGTH: 89
<212> TYPE: PRT
<213> ORGANISM: Bos taurus

<400> SEQUENCE: 14

```
Met Asp Ala Lys Val Phe Val Val Leu Ala Leu Val Leu Thr Ala Leu
1               5                   10                  15

Cys Leu Ser Asp Ala Lys Pro Val Ser Leu Ser Tyr Arg Cys Pro Cys
            20                  25                  30

Arg Phe Phe Glu Ser His Val Ala Lys Ala Asn Val Lys His Leu Lys
        35                  40                  45

Ile Leu Asn Thr Pro Asn Cys Ser Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Asp Lys Ala Leu Asn Lys
                85
```

<210> SEQ ID NO 15
<211> LENGTH: 270
<212> TYPE: DNA
<213> ORGANISM: Homo sapiens

<400> SEQUENCE: 15

```
atgaacgcca aggtcgtggt cgtgctggtc ctcgtgctga ccgcgctctg cctcagcgac      60
gggaagcccg tcagcctgag ctacagatgc ccatgccgat tcttcgaaag ccatgttgcc     120
agagccaacg tcaagcatct caaaattctc aacactccaa actgtgccct tcagattgta     180
gcccggctga gaacaacaa cagacaagtg tgcattgacc cgaagctaaa gtggattcag      240
gagtacctgg agaaagcttt aaacaagtaa                                      270
```

<210> SEQ ID NO 16
<211> LENGTH: 89
<212> TYPE: PRT
<213> ORGANISM: Homo sapiens

<400> SEQUENCE: 16

```
Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
```

```
                    50                  55                  60
Asn Asn Asn Arg Gln Val Cys Ile Asp Pro Lys Leu Lys Trp Ile Gln
 65                  70                  75                  80

Glu Tyr Leu Glu Lys Ala Leu Asn Lys
                 85

<210> SEQ ID NO 17
<211> LENGTH: 270
<212> TYPE: DNA
<213> ORGANISM: Mus musculus

<400> SEQUENCE: 17
atggacgcca aggtcgtcgc cgtgctggcc ctggtgctgg ccgcgctctg catcagtgac    60
ggtaaaccag tcagcctgag ctaccgatgc ccctgccggt tcttcgagag ccacatcgcc   120
agagccaacg tcaagcatct gaaaatcctc aacactccaa actgtgccct tcagattgtt   180
gcacggctga agaacaacaa cagacaagtg tgcattgacc cgaaattaaa gtggatccaa   240
gagtacctgg agaaagcttt aaacaagtaa                                    270

<210> SEQ ID NO 18
<211> LENGTH: 89
<212> TYPE: PRT
<213> ORGANISM: Mus musculus

<400> SEQUENCE: 18

Met Asp Ala Lys Val Val Ala Val Leu Ala Leu Val Leu Ala Ala Leu
 1               5                  10                  15

Cys Ile Ser Asp Gly Lys Pro Val Ser Leu Ser Tyr Arg Cys Pro Cys
                 20                  25                  30

Arg Phe Phe Glu Ser His Ile Ala Arg Ala Asn Val Lys His Leu Lys
             35                  40                  45

Ile Leu Asn Thr Pro Asn Cys Ala Leu Gln Ile Val Ala Arg Leu Lys
         50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Lys
                 85

<210> SEQ ID NO 19
<211> LENGTH: 819
<212> TYPE: DNA
<213> ORGANISM: Gallus gallus

<400> SEQUENCE: 19
atgaatgaag cctacagccc tgcagcacct cgacccatgg gcagcacctc tcccagcacc    60
atgaaaatgt ttatgtgctt cctctctgta ttcatggtgg tacagaccat tgggaccgta   120
ctcttctgtt tatatcttca catgaagatg gataagatgg aagaggtgtt gagtttaaat   180
gaagattaca tctttctgag aaaagtgcag aaatgtcaga cggagaagaa tcagaagtcg   240
acattattgg actgtgaaaa agttctaaaa ggcttccagg acctccaatg caaggatagg   300
acagccagtg aggagttgcc aaaatttgaa atgcacagag tcatgagca ccccacttg    360 aagagtagga atgagacatc tgtggcagag agaagaggc agccgatcgc aacacacctg   420
gcaggggtga agagcaacac aacagtgaga gtgctgaagt ggatgacgac gagctacgcc   480
ccaacgagca gcttgatatc ctaccatgag gggaagctga aggtggagaa agcagggctc   540
tactacatct actcacaagt cagcttctgc accaaggcgg cggcttcggc gccattcacc   600
```
ctctatattt atttgtacct ccccatggaa gaggaccggc tcctgatgaa gggacttgac    660
acgcacagca cctccacggc tctctgtgag ctccagtcca tccgggaggg cggtgtcttc    720
gagctgcggc agggcgacat ggtctttgtc aatgtgacgg actcaacagc agtgaacgtc    780
aaccctggca cacctactt tggcatgttc aagctgtag                           819

<210> SEQ ID NO 20
<211> LENGTH: 272
<212> TYPE: PRT
<213> ORGANISM: Gallus gallus

<400> SEQUENCE: 20

Met Asn Glu Ala Tyr Ser Pro Ala Ala Pro Arg Pro Met Gly Ser Thr
1               5                   10                  15

Ser Pro Ser Thr Met Lys Met Phe Met Cys Phe Leu Ser Val Phe Met
            20                  25                  30

Val Val Gln Thr Ile Gly Thr Val Leu Phe Cys Leu Tyr Leu His Met
        35                  40                  45

Lys Met Asp Lys Met Glu Glu Val Leu Ser Leu Asn Glu Asp Tyr Ile
    50                  55                  60

Phe Leu Arg Lys Val Gln Lys Cys Gln Thr Gly Glu Asp Gln Lys Ser
65                  70                  75                  80

Thr Leu Leu Asp Cys Glu Lys Val Leu Lys Gly Phe Gln Asp Leu Gln
                85                  90                  95

Cys Lys Asp Arg Thr Ala Ser Glu Glu Leu Pro Lys Phe Glu Met His
            100                 105                 110

Arg Gly His Glu His Pro His Leu Lys Ser Arg Asn Glu Thr Ser Val
        115                 120                 125

Ala Glu Glu Lys Arg Gln Pro Ile Ala Thr His Leu Ala Gly Val Lys
    130                 135                 140

Ser Asn Thr Thr Val Arg Val Leu Lys Trp Met Thr Thr Ser Tyr Ala
145                 150                 155                 160

Pro Thr Ser Ser Leu Ile Ser Tyr His Glu Gly Lys Leu Lys Val Glu
                165                 170                 175

Lys Ala Gly Leu Tyr Tyr Ile Tyr Ser Gln Val Ser Phe Cys Thr Lys
            180                 185                 190

Ala Ala Ala Ser Ala Pro Phe Thr Leu Tyr Ile Tyr Leu Tyr Leu Pro
        195                 200                 205

Met Glu Glu Asp Arg Leu Leu Met Lys Gly Leu Asp Thr His Ser Thr
    210                 215                 220

Ser Thr Ala Leu Cys Glu Leu Gln Ser Ile Arg Glu Gly Gly Val Phe
225                 230                 235                 240

Glu Leu Arg Gln Gly Asp Met Val Phe Val Asn Val Thr Asp Ser Thr
                245                 250                 255

Ala Val Asn Val Asn Pro Gly Asn Thr Tyr Phe Gly Met Phe Lys Leu
            260                 265                 270

<210> SEQ ID NO 21
<211> LENGTH: 786
<212> TYPE: DNA
<213> ORGANISM: Sus scrofa

<400> SEQUENCE: 21
atgatcgaaa cgtacagcca accttcgccc cgctctgtgg ccgctggacc acccgtcagt    60
atgaaaatct ttatgtattt acttactgtt tttcttatca cccagatgat tgggtcagca    120

```
cttttttgcag cgtaccttca cagaagattg acaagatag aagatgaaag gaatcttcat    180
gaagattttg tgttcataaa aacgatacag agatgcaagc aaggagaggg gtccttatcc    240
ttattgaact gtgaggaaat cagaagccag tttgaagacc tggtcaaggg tataatgcaa    300
agcaaagaag tgaagaagaa agaaaaaagc tttgaaatgc acaaaggcga tcaggatcct    360
caaattgcgg cacatgtcat aagcgaggcc agtagtaaaa cagcatctgt cctgcagtgg    420 gccccccaaag ggtactacac cctcagcacc aacttggtga ccctggaaaa cgggagacag    480
ctggccgtca aaagacaagg aatctattac atctacgccc aagtcacctt ctgctccaac    540
cgggacgccg cgggtcaagc tcccttcata gccagcctct gcctgaggtc ccaagcggg    600 tcggagagaa tcttactccg cgcggccaac acccacagtt cctccaagcc ctgcgggcag    660
caatccattc acttgggcgg agtcttcgag ttgcaacccg gcgcttcggt gttcgtcaac    720
gtgactgatc caagccaagt gagccacggg accggcttca cgtcttttgg cctcctcaaa    780
ctctga                                                               786
```

<210> SEQ ID NO 22
<211> LENGTH: 261
<212> TYPE: PRT
<213> ORGANISM: Sus scrofa

<400> SEQUENCE: 22

```
Met Ile Glu Thr Tyr Ser Gln Pro Ser Pro Arg Ser Val Ala Ala Gly
1               5                   10                  15

Pro Pro Val Ser Met Lys Ile Phe Met Tyr Leu Leu Thr Val Phe Leu
            20                  25                  30

Ile Thr Gln Met Ile Gly Ser Ala Leu Phe Ala Ala Tyr Leu His Arg
        35                  40                  45

Arg Leu Asp Lys Ile Glu Asp Glu Arg Asn Leu His Glu Asp Phe Val
    50                  55                  60

Phe Ile Lys Thr Ile Gln Arg Cys Lys Gln Gly Glu Gly Ser Leu Ser
65                  70                  75                  80

Leu Leu Asn Cys Glu Glu Ile Arg Ser Gln Phe Glu Asp Leu Val Lys
                85                  90                  95

Gly Ile Met Gln Ser Lys Glu Val Lys Lys Glu Lys Ser Phe Glu
            100                 105                 110

Met His Lys Gly Asp Gln Asp Pro Gln Ile Ala Ala His Val Ile Ser
        115                 120                 125

Glu Ala Ser Ser Lys Thr Ala Ser Val Leu Gln Trp Ala Pro Lys Gly
    130                 135                 140

Tyr Tyr Thr Leu Ser Thr Asn Leu Val Thr Leu Glu Asn Gly Arg Gln
145                 150                 155                 160

Leu Ala Val Lys Arg Gln Gly Ile Tyr Tyr Ile Tyr Ala Gln Val Thr
                165                 170                 175

Phe Cys Ser Asn Arg Asp Ala Ala Gly Gln Ala Pro Phe Ile Ala Ser
            180                 185                 190

Leu Cys Leu Arg Ser Pro Ser Gly Ser Glu Arg Ile Leu Leu Arg Ala
        195                 200                 205

Ala Asn Thr His Ser Ser Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
```

Gly Leu Leu Lys Leu
        260

<210> SEQ ID NO 23
<211> LENGTH: 786
<212> TYPE: DNA
<213> ORGANISM: Bos taurus

<400> SEQUENCE: 23

```
atgatcgaaa catacagtca accttctccc cgctccgtgg ccactggacc acctgtcagt      60
atgaaaattt ttatgtattt acttacagtt tttcttatca cccagatgat tgggtcagcg     120
cttttgctg tgtatcttca cagacgattg acaagatag aagacgaaag gaatcttcat      180
gaagattttg tgttcatgaa aacgatacag agatgcaata aaggagaggg gtccttatcc     240
ttactgaact gtgaggaaat tagaagccgg tttgaagact tggtcaagga tataatgcaa     300
aacaaagaag taagaagaa agaaaaaaac tttgaaatgc acaagggtga tcaggagcct     360
cagatagcgg cacatgtcat cagtgaggcc agtagtaaaa caacctctgt tctccagtgg     420
gccccccaaag gatactacac cctaagcaac aacctggtaa ccctcgaaaa cgggaaacag     480
ctggccgtga aaagacaagg attctattac atctacaccc aagtcacctt ctgttccaat     540
cgggaaactt tgagtcaagc tccatttata gccagcctct gcctgaagtc cccaagtgga     600
tcagagagaa tcttactgag agctgcaaac acccacagtt cttccaaacc atgcgggcag     660
caatccattc acttaggagg agtctttgaa ttgcaatcgg gtgcttcggt gtttgtcaat     720
gtgactgatc caagtcaagt gagccacggg acgggcttca catcatttgg cttactcaaa     780
ctctga                                                                786
```

<210> SEQ ID NO 24
<211> LENGTH: 261
<212> TYPE: PRT
<213> ORGANISM: Bos taurus

<400> SEQUENCE: 24

Met Ile Glu Thr Tyr Ser Gln Pro Ser Pro Arg Ser Val Ala Thr Gly
1               5                   10                  15

Pro Pro Val Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Lys Gly Glu Gly Ser Leu Ser
65                  70                  75                  80

Leu Leu Asn Cys Glu Glu Ile Arg Ser Arg Phe Glu Asp Leu Val Lys
                85                  90                  95

Asp Ile Met Gln Asn Lys Glu Val Lys Lys Glu Lys Asn Phe Glu
            100                 105                 110

Met His Lys Gly Asp Gln Glu Pro Gln Ile Ala Ala His Val Ile Ser
        115                 120                 125

Glu Ala Ser Ser Lys Thr Thr Ser Val Leu Gln Trp Ala Pro Lys Gly
    130                 135                 140

Tyr Tyr Thr Leu Ser Asn Asn Leu Val Thr Leu Glu Asn Gly Lys Gln
145                 150                 155                 160

-continued

```
Leu Ala Val Lys Arg Gln Gly Phe Tyr Tyr Ile Tyr Thr Gln Val Thr
            165                 170                 175

Phe Cys Ser Asn Arg Glu Thr Leu Ser Gln Ala Pro Phe Ile Ala Ser
        180                 185                 190

Leu Cys Leu Lys Ser Pro Ser Gly Ser Glu Arg Ile Leu Leu Arg Ala
    195                 200                 205

Ala Asn Thr His Ser Ser Lys Pro Cys Gly Gln Gln Ser Ile His
210                 215                 220

Leu Gly Gly Val Phe Glu Leu Gln Ser Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 25
<211> LENGTH: 786
<212> TYPE: DNA
<213> ORGANISM: Homo sapiens

<400> SEQUENCE: 25
atgatcgaaa catacaacca aacttctccc cgatctgcgg ccactggact gcccatcagc      60
atgaaaattt ttatgtattt acttactgtt tttcttatca cccagatgat tgggtcagca     120 cttttgctg tgtatcttca tagaaggttg gacaagatag aagatgaaag gaatcttcat     180
gaagattttg tattcatgaa aacgatacag agatgcaaca caggagaaag atccttatcc     240
ttactgaact gtgaggagat taaaagccag tttgaaggct tgtgaagga tataatgtta     300 aacaaagagg agacgaagaa agaaaacagc tttgaaatgc aaaaaggtga tcagaatcct     360
caaattgcgg cacatgtcat aagtgaggcc agcagtaaaa caacatctgt gttacagtgg     420
gctgaaaaag gatactacac catgagcaac aacttggtaa ccctggaaaa tgggaaacag     480
ctgaccgtta aaagacaagg actctattat atctatgccc aagtcacctt ctgttccaat     540
cgggaagctt cgagtcaagc tccatttata gccagcctct gcctaaagtc ccccggtaga     600
ttcgagagaa tcttactcag agctgcaaat acccacagtt ccgccaaacc ttgcgggcaa     660
caatccattc acttgggagg agtatttgaa ttgcaaccag gtgcttcggt gtttgtcaat     720
gtgactgatc caagccaagt gagccatggc actggcttca cgtcctttgg cttactcaaa     780
ctctga                                                                786

<210> SEQ ID NO 26
<211> LENGTH: 261
<212> TYPE: PRT
<213> ORGANISM: Homo sapiens

<400> SEQUENCE: 26

Met Ile Glu Thr Tyr Asn Gln Thr Ser Pro Arg Ser Ala Ala Thr Gly
1               5                  10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80
```

Leu Leu Asn Cys Glu Glu Ile Lys Ser Gln Phe Gly Phe Val Lys
                85                  90                  95

Asp Ile Met Leu Asn Lys Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 27
<211> LENGTH: 783
<212> TYPE: DNA
<213> ORGANISM: Mus musculus

<400> SEQUENCE: 27
atgatagaaa catacagcca accttccccc agatccgtgg caactggact tccagcgagc      60
atgaagattt ttatgtattt acttactgtt ttccttatca cccaaatgat tggatctgtg     120 cttttttgctg tgtatcttca tagaagattg gataaggtcg aagaggaagt aaaccttcat    180
gaagattttg tattcataaa aaagctaaag agatgcaaca aggagaagg atctttatcc     240 ttgctgaact gtgaggagat gagaaggcaa tttgaagacc ttgtcaagga tataacgtta    300
aacaaagaag agaaaaaaga aacagctttg aaatgcaaa gaggtgatga ggatcctcaa     360
attgcagcac acgttgtaag cgaagccaac agtaatgcag catccgttct acagtgggcc    420
aagaaaggat attataccat gaaaagcaac ttggtaatgc ttgaaaatgg aaacagctg     480 acggttaaaa gagaaggact ctattatgtc tacactcaag tcaccttctg ctctaatcgg    540
gagccttcga gtcaacgccc attcatcgtc ggcctctggc tgaagcccag cagtggatct    600
gagagaatct tactcaaggc ggcaaatacc cacagttcct cccagctttg cgagcagcag    660
tctgttcact gggcggagt gtttgaatta caagctggtg cttctgtgtt tgtcaacgtg     720
actgaagcaa gccaagtgat ccacagagtt ggcttctcat cttttggctt actcaaactc    780
tga                                                                   783

<210> SEQ ID NO 28
<211> LENGTH: 260
<212> TYPE: PRT
<213> ORGANISM: Mus musculus

<400> SEQUENCE: 28

```
Met Ile Glu Thr Tyr Ser Gln Pro Ser Pro Arg Ser Val Ala Thr Gly
1               5                   10                  15
Leu Pro Ala Ser Met Lys Ile Phe Met Tyr Leu Leu Thr Val Phe Leu
            20                  25                  30
Ile Thr Gln Met Ile Gly Ser Val Leu Phe Ala Val Tyr Leu His Arg
        35                  40                  45
Arg Leu Asp Lys Val Glu Glu Val Asn Leu His Glu Asp Phe Val
    50                  55                  60
Phe Ile Lys Lys Leu Lys Arg Cys Asn Lys Gly Gly Ser Leu Ser
65                  70                  75                  80
Leu Leu Asn Cys Glu Glu Met Arg Arg Gln Phe Glu Asp Leu Val Lys
            85                  90                  95
Asp Ile Thr Leu Asn Lys Glu Glu Lys Glu Asn Ser Phe Glu Met
        100                 105                 110
Gln Arg Gly Asp Glu Asp Pro Gln Ile Ala Ala His Val Val Ser Glu
    115                 120                 125
Ala Asn Ser Asn Ala Ala Ser Val Leu Gln Trp Ala Lys Lys Gly Tyr
    130                 135                 140
Tyr Thr Met Lys Ser Asn Leu Val Met Leu Glu Asn Gly Lys Gln Leu
145                 150                 155                 160
Thr Val Lys Arg Glu Gly Leu Tyr Tyr Val Tyr Thr Gln Val Thr Phe
                165                 170                 175
Cys Ser Asn Arg Glu Pro Ser Ser Gln Arg Pro Phe Ile Val Gly Leu
            180                 185                 190
Trp Leu Lys Pro Ser Ser Gly Ser Glu Arg Ile Leu Leu Lys Ala Ala
        195                 200                 205
Asn Thr His Ser Ser Ser Gln Leu Cys Glu Gln Gln Ser Val His Leu
    210                 215                 220
Gly Gly Val Phe Glu Leu Gln Ala Gly Ala Ser Val Phe Val Asn Val
225                 230                 235                 240
Thr Glu Ala Ser Gln Val Ile His Arg Val Gly Phe Ser Ser Phe Gly
                245                 250                 255
Leu Leu Lys Leu
        260
```

<210> SEQ ID NO 29
<211> LENGTH: 429
<212> TYPE: DNA
<213> ORGANISM: Gallus gallus

<400> SEQUENCE: 29

```
atgatgtgca aagtactgat ctttggctgt atttcggtag caatgctaat gactacagct      60
tatggagcat ctctatcatc agcaaaaagg aaacctcttc aaacattaat aaaggattta     120
gaaatattgg aaaatatcaa gaacattcat ctcgagctct acaccaac tgagacccag       180
gagtgcaccc agcaaactct gcagtgttac ctgggagaag tggttactct gaagaaagaa     240
actgaagatg acactgaaat taagaagaa tttgtaactg ctattcaaaa tatcgataag      300
aacctcaaga gtcttacggg tctaaatcac accggaagtg aatgcaaggt ctgtgaagct     360
aacaacaaga aaaaatttcc tgattttctc catgaactga ccaactttgt gagatatctg     420
caaaaataa                                                             429
```

<210> SEQ ID NO 30

```
<211> LENGTH: 142
<212> TYPE: PRT
<213> ORGANISM: Gallus gallus

<400> SEQUENCE: 30

Met Met Cys Lys Val Leu Ile Phe Gly Cys Ile Ser Val Ala Met Leu
1               5                   10                  15

Met Thr Thr Ala Tyr Gly Ala Ser Leu Ser Ser Ala Lys Arg Lys Pro
            20                  25                  30

Leu Gln Thr Leu Ile Lys Asp Leu Glu Ile Leu Glu Asn Ile Lys Asn
        35                  40                  45

Ile His Leu Glu Leu Tyr Thr Pro Thr Glu Thr Gln Glu Cys Thr Gln
    50                  55                  60

Gln Thr Leu Gln Cys Tyr Leu Gly Glu Val Val Thr Leu Lys Lys Glu
65                  70                  75                  80

Thr Glu Asp Asp Thr Glu Ile Lys Glu Glu Phe Val Thr Ala Ile Gln
                85                  90                  95

Asn Ile Asp Lys Asn Leu Lys Ser Leu Thr Gly Leu Asn His Thr Gly
            100                 105                 110

Ser Glu Cys Lys Val Cys Glu Ala Asn Asn Lys Lys Phe Pro Asp
        115                 120                 125

Phe Leu His Glu Leu Thr Asn Phe Val Arg Tyr Leu Gln Lys
    130                 135                 140

<210> SEQ ID NO 31
<211> LENGTH: 465
<212> TYPE: DNA
<213> ORGANISM: Sus scrofa

<400> SEQUENCE: 31
atgtataaga tgcagctctt gtgttgcatt gcactaaccc ttgcactcat ggcaaacggt      60
gcacctactt caagctctac aaagaacaca aagaaacaac tggagccatt gctgctggat     120
ttacagttgc ttttgaagga agttaagaat tacgagaatg ctgatctctc caggatgctc     180
acatttaaat tttacatgcc caagcaggct acagaattga acaccttca gtgtttagta      240 gaagaactca aagctctgga gggagtgcta aatttaggtc aaagcaaaaa ctctgactca     300
gcaaatatca aggaatcaat gaacaatatc aacgtaacag ttttggaact aaagggatct     360
gaaacaagtt tcgaatgtga atatgatgat gagacagtaa ctgctgttga atttctgaac     420
aaatggatta ccttttgtca aagcatctac tcaacactga cttga                     465

<210> SEQ ID NO 32
<211> LENGTH: 154
<212> TYPE: PRT
<213> ORGANISM: Sus scrofa

<400> SEQUENCE: 32

Met Tyr Lys Met Gln Leu Leu Cys Cys Ile Ala Leu Thr Leu Ala Leu
1               5                   10                  15

Met Ala Asn Gly Ala Pro Thr Ser Ser Ser Thr Lys Asn Thr Lys Lys
            20                  25                  30

Gln Leu Glu Pro Leu Leu Leu Asp Leu Gln Leu Leu Lys Glu Val
        35                  40                  45

Lys Asn Tyr Glu Asn Ala Asp Leu Ser Arg Met Leu Thr Phe Lys Phe
    50                  55                  60

Tyr Met Pro Lys Gln Ala Thr Glu Leu Lys His Leu Gln Cys Leu Val
65                  70                  75                  80
```

Glu Glu Leu Lys Ala Leu Glu Gly Val Leu Asn Leu Gly Gln Ser Lys
                85                  90                  95

Asn Ser Asp Ser Ala Asn Ile Lys Glu Ser Met Asn Asn Ile Asn Val
            100                 105                 110

Thr Val Leu Glu Leu Lys Gly Ser Glu Thr Ser Phe Glu Cys Glu Tyr
        115                 120                 125

Asp Asp Glu Thr Val Thr Ala Val Glu Phe Leu Asn Lys Trp Ile Thr
    130                 135                 140

Phe Cys Gln Ser Ile Tyr Ser Thr Leu Thr
145                 150

<210> SEQ ID NO 33
<211> LENGTH: 405
<212> TYPE: DNA
<213> ORGANISM: Bos taurus

<400> SEQUENCE: 33
gcacctactt caagctctac ggggaacaca atgaaagaag tgaagtcatt gctgctggat      60
ttacagttgc ttttggagaa agttaaaaat cctgagaacc tcaagctctc aggatgcat      120 acatttgact tttacgcgcc caaggttaac gctacgaat gaaacatct taagtgttta       180 ctagaagaac tcaaacttct agaggaagtg ctaaatttag ctccaagcaa aacttgaac      240 cccagagaga tcaaggattc aatggacaat atcaagaga tcgttttgga actacaggga      300
tctgaaacaa gattcacatg tgaatatgat gatgcaacag taaacgctgt agaatttctg      360
aacaaatgga ttaccttttg tcaaagcatc tactcaacaa tgact                     405

<210> SEQ ID NO 34
<211> LENGTH: 135
<212> TYPE: PRT
<213> ORGANISM: Bos taurus

<400> SEQUENCE: 34

Ala Pro Thr Ser Ser Thr Gly Asn Thr Met Lys Glu Val Lys Ser
1               5                   10                  15

Leu Leu Leu Asp Leu Gln Leu Leu Leu Glu Lys Val Lys Asn Pro Glu
            20                  25                  30

Asn Leu Lys Leu Ser Arg Met His Thr Phe Asp Phe Tyr Ala Pro Lys
        35                  40                  45

Val Asn Ala Thr Glu Leu Lys His Leu Lys Cys Leu Leu Glu Glu Leu
    50                  55                  60

Lys Leu Leu Glu Glu Val Leu Asn Leu Ala Pro Ser Lys Asn Leu Asn
65                  70                  75                  80

Pro Arg Glu Ile Lys Asp Ser Met Asp Asn Ile Lys Arg Ile Val Leu
                85                  90                  95

Glu Leu Gln Gly Ser Glu Thr Arg Phe Thr Cys Glu Tyr Asp Asp Ala
            100                 105                 110

Thr Val Asn Ala Val Glu Phe Leu Asn Lys Trp Ile Thr Phe Cys Gln
        115                 120                 125

Ser Ile Tyr Ser Thr Met Thr
    130                 135

<210> SEQ ID NO 35
<211> LENGTH: 462
<212> TYPE: DNA
<213> ORGANISM: Homo sapiens

<400> SEQUENCE: 35

```
atgtacagga tgcaactcct gtcttgcatt gcactaagtc ttgcacttgt cacaaacagt      60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc caagaaggcc acagaactga acatcttca gtgtctagaa     240
gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt tctgaacaga    420
tggattacct tttgtcaaag catcatctca acactgactt ga                       462
```

<210> SEQ ID NO 36
<211> LENGTH: 153
<212> TYPE: PRT
<213> ORGANISM: Homo sapiens

<400> SEQUENCE: 36

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 37
<211> LENGTH: 500
<212> TYPE: DNA
<213> ORGANISM: Mus musculus

<400> SEQUENCE: 37

```
atgcagctcg catcctgtgt cacattgaca cttgtgctcc ttgtcaacag cgcacccact      60
tcaagctcca cttcaagctc tacagcggaa gcacagcagc agcagcagca gcagcagcag    120
cagcagcagc acctggagca gctgttgatg gacctacagg agctcctgag caggatggag    180
aattacagga acctgaaact ccccaggatg ctcaccttca attttactt gcccaagcag     240
gccacagaat tgaaagatct tcagtgccta gaagatgaac ttggacctct gcggcatgtt    300
ctggatttga ctcaaagcaa aagctttcaa ttggaagatg ctgagaattt catcagcaat    360
atcagagtaa ctgttgtaaa actaaagggc tctgacaaca catttgagtg ccaattcgat    420
gatgagtcag caactgtggt ggactttctg aggagatgga tagccttctg tcaaagcatc    480
```
atctcaacaa gccctcaata 500

<210> SEQ ID NO 38
<211> LENGTH: 169
<212> TYPE: PRT
<213> ORGANISM: Mus musculus

<400> SEQUENCE: 38

```
Met Tyr Ser Met Gln Leu Ala Ser Cys Val Thr Leu Thr Leu Val Leu
1               5                   10                  15
Leu Val Asn Ser Ala Pro Thr Ser Ser Thr Ser Ser Ser Thr Ala
            20                  25                  30
Glu Ala Gln Gln Gln Gln Gln Gln Gln Gln Gln Gln Gln His Leu
        35                  40                  45
Glu Gln Leu Leu Met Asp Leu Gln Glu Leu Leu Ser Arg Met Glu Asn
    50                  55                  60
Tyr Arg Asn Leu Lys Leu Pro Arg Met Leu Thr Phe Lys Phe Tyr Leu
65                  70                  75                  80
Pro Lys Gln Ala Thr Glu Leu Lys Asp Leu Gln Cys Leu Glu Asp Glu
                85                  90                  95
Leu Gly Pro Leu Arg His Val Leu Asp Leu Thr Gln Ser Lys Ser Phe
            100                 105                 110
Gln Leu Glu Asp Ala Glu Asn Phe Ile Ser Asn Ile Arg Val Thr Val
        115                 120                 125
Val Lys Leu Lys Gly Ser Asp Asn Thr Phe Glu Cys Gln Phe Asp Asp
    130                 135                 140
Glu Ser Ala Thr Val Val Asp Phe Leu Arg Arg Trp Ile Ala Phe Cys
145                 150                 155                 160
Gln Ser Ile Ile Ser Thr Ser Pro Gln
                165
```

<210> SEQ ID NO 39
<211> LENGTH: 672
<212> TYPE: DNA
<213> ORGANISM: Artificial Sequence
<220> FEATURE:
<223> OTHER INFORMATION: Nucleotide sequence of fusion protein

<400> SEQUENCE: 39
gctctgtcgc aaggtaggac gctggtaaag atggggaatg agctgcggtg ccagtgcatt     60
agcactcatt ctaagttcat ccaccctaaa tccattcaag atgtgaagct gacgccaagc    120
ggcccccact gcaagaatgt tgaaatcata gctactctaa aggatggaag agaggtgtgc    180
ttgaacccca ctgctccctg ggtacagctg atcgtaaagg cacttatggc caaggctcag    240
ctcaattctg atgcaccact ggaagctgcg gcaaaagagg cagctgcgaa ggaagcggca    300
gcgaaagcat ctctatcatc agcgaaaagg aaacctcttc aaacattaat aaaggattta    360
gaaatattgg aaaatatcaa gaacaagatt catctcgagc tctacacacc aactgagacc    420
caggagtgca cccagcaaac tctgcagtgt tacctgggag aagtggttac tctgaagaaa    480
gaaactgaag atgacactga aattaaagaa gaatttgtaa ctgctattca aaatatcgaa    540
aagaacctca agagtcttac gggtctaaat cacaccggaa gtgaatgcaa gatctgtgaa    600
gctaacaaca gaaaaaaatt tcctgatttt ctccatgaac tgaccaactt tgtgagatat    660
ctgcaaaaat aa                                                        672

-continued

```
<210> SEQ ID NO 40
<211> LENGTH: 223
<212> TYPE: PRT
<213> ORGANISM: Artificial Sequence
<220> FEATURE:
<223> OTHER INFORMATION: Amino acid sequence of fusion protein

<400> SEQUENCE: 40

Ala Leu Ser Gln Gly Arg Thr Leu Val Lys Met Gly Asn Glu Leu Arg
1               5                   10                  15

Cys Gln Cys Ile Ser Thr His Ser Lys Phe Ile His Pro Lys Ser Ile
            20                  25                  30

Gln Asp Val Lys Leu Thr Pro Ser Gly Pro His Cys Lys Asn Val Glu
        35                  40                  45

Ile Ile Ala Thr Leu Lys Asp Gly Arg Glu Val Cys Leu Asn Pro Thr
    50                  55                  60

Ala Pro Trp Val Gln Leu Ile Val Lys Ala Leu Met Ala Lys Ala Gln
65                  70                  75                  80

Leu Asn Ser Asp Ala Pro Leu Glu Ala Ala Lys Glu Ala Ala
                85                  90                  95

Lys Glu Ala Ala Ala Lys Ala Ser Leu Ser Ser Ala Lys Arg Lys Pro
            100                 105                 110

Leu Gln Thr Leu Ile Lys Asp Leu Glu Ile Leu Glu Asn Ile Lys Asn
        115                 120                 125

Lys Ile His Leu Glu Leu Tyr Thr Pro Thr Glu Thr Gln Glu Cys Thr
    130                 135                 140

Gln Gln Thr Leu Gln Cys Tyr Leu Gly Glu Val Val Thr Leu Lys Lys
145                 150                 155                 160

Glu Thr Glu Asp Asp Thr Glu Ile Lys Glu Glu Phe Val Thr Ala Ile
                165                 170                 175

Gln Asn Ile Glu Lys Asn Leu Lys Ser Leu Thr Gly Leu Asn His Thr
            180                 185                 190

Gly Ser Glu Cys Lys Ile Cys Glu Ala Asn Asn Lys Lys Lys Phe Pro
        195                 200                 205

Asp Phe Leu His Glu Leu Thr Asn Phe Val Arg Tyr Leu Gln Lys
    210                 215                 220

<210> SEQ ID NO 41
<211> LENGTH: 990
<212> TYPE: DNA
<213> ORGANISM: Artificial Sequence
<220> FEATURE:
<223> OTHER INFORMATION: Nucleotide sequence of fusion protein

<400> SEQUENCE: 41
gctctgtcgc aaggtaggac gctggtaaag atggggaatg agctgcggtg ccagtgcatt      60
agcactcatt ctaagttcat ccaccctaaa tccattcaag atgtgaagct gacgccaagc     120 ggccccact gcaagaatgt tgaaatcata gctactctaa aggatggaag agaggtgtgc     180
ttgaacccca ctgctcccctg gtacagctg atcgtaaagg cacttatggc caaggctcag     240
ctcaattctg atgcaccact ggaagctgcg gcaaaagagg cagctgcgaa ggaagcggca     300
gcgaaacaca tgaagatgga taagatgaa gaggtgttga gtttaaatga agattacatc     360
tttctgagaa aagtgcagaa atgtcagacg ggagaagatc agaagtcgac attattggac     420
tgtgaaaaag ttctaaaagg cttccaggac ctccaatgca gggataggac agccagtgag     480
gagttgccaa aatttgaaat gcacagaggt catgagcacc cccacttgaa gagtaggaat     540
```

```
gagacatctg tggcagagga gaagaggcag ccgatcgcaa cacacctggc aggggtgaag    600
agcaacacaa cagtgagagt gctgaagtgg atgacgacgg gctacgcccc aacgagcagc    660
ttgatatcct accatgaggg gaagctgaag gtggagaaag cagggctcta ctacatctac    720
tcacaagtca gcttctgcac caaggcggcg gcttcggcgc cattcaccct ctatatttat    780
ttgtacctcc ccatggaaga ggaccggctc ctgatgaagg gacttgacac gcacagcacc    840
tccacggctc tctgtgagct ccagtccatc cgggagggcg tgtcttcga gctgcggcag    900 ggcgacatgg actttgtcaa tgtgacggac tcaacagcag tgaacgtcaa ccctggcaac    960
acctactttg gcatgttcaa gctgtagtaa                                     990
```

```
<210> SEQ ID NO 42
<211> LENGTH: 328
<212> TYPE: PRT
<213> ORGANISM: Artificial Sequence
<220> FEATURE:
<223> OTHER INFORMATION: Amino acid sequence of fusion protein

<400> SEQUENCE: 42

Ala Leu Ser Gln Gly Arg Thr Leu Val Lys Met Gly Asn Glu Leu Arg
1               5                   10                  15

Cys Gln Cys Ile Ser Thr His Ser Lys Phe Ile His Pro Lys Ser Ile
            20                  25                  30

Gln Asp Val Lys Leu Thr Pro Ser Gly Pro His Cys Lys Asn Val Glu
        35                  40                  45

Ile Ile Ala Thr Leu Lys Asp Gly Arg Glu Val Cys Leu Asn Pro Thr
    50                  55                  60

Ala Pro Trp Val Gln Leu Ile Val Lys Ala Leu Met Ala Lys Ala Gln
65                  70                  75                  80

Leu Asn Ser Asp Ala Pro Leu Glu Ala Ala Ala Lys Glu Ala Ala Ala
                85                  90                  95

Lys Glu Ala Ala Ala Lys His Met Lys Met Asp Lys Met Glu Glu Val
            100                 105                 110

Leu Ser Leu Asn Glu Asp Tyr Ile Phe Leu Arg Lys Val Gln Lys Cys
        115                 120                 125

Gln Thr Gly Glu Asp Gln Lys Ser Thr Leu Leu Asp Cys Glu Lys Val
    130                 135                 140

Leu Lys Gly Phe Gln Asp Leu Gln Cys Arg Asp Arg Thr Ala Ser Glu
145                 150                 155                 160

Glu Leu Pro Lys Phe Glu Met His Arg Gly His Glu His Pro His Leu
                165                 170                 175

Lys Ser Arg Asn Glu Thr Ser Val Ala Glu Glu Lys Arg Gln Pro Ile
            180                 185                 190

Ala Thr His Leu Ala Gly Val Lys Ser Asn Thr Thr Val Arg Val Leu
        195                 200                 205

Lys Trp Met Thr Thr Ser Tyr Ala Pro Thr Ser Ser Leu Ile Ser Tyr
    210                 215                 220

His Glu Gly Lys Leu Lys Val Glu Lys Ala Gly Leu Tyr Tyr Ile Tyr
225                 230                 235                 240

Ser Gln Val Ser Phe Arg Thr Lys Ala Ala Ser Ala Pro Phe Thr
                245                 250                 255

Leu Tyr Ile Tyr Leu Tyr Leu Pro Met Glu Glu Asp Arg Leu Leu Met
            260                 265                 270

Lys Gly Leu Asp Thr His Ser Ala Ser Thr Ala Leu Cys Glu Leu Gln
        275                 280                 285
```

```
Ser Ile Arg Glu Gly Gly Val Phe Glu Leu Arg Gln Gly Asp Met Val
    290                 295                 300
Phe Val Asn Val Thr Asp Ser Thr Ala Val Asn Val Asn Pro Gly Asn
305                 310                 315                 320
Thr Tyr Phe Gly Met Phe Lys Leu
                325
```

```
<210> SEQ ID NO 43
<211> LENGTH: 615
<212> TYPE: DNA
<213> ORGANISM: Artificial Sequence
<220> FEATURE:
<223> OTHER INFORMATION: Nucleotide sequence of fusion protein

<400> SEQUENCE: 43
aagcctgtca gcctgactta ccgatgcccc tgtcgattct tcgagagcaa cgtggcgagg    60
gccaacatta gcacctcaa atccttttcc actcccaact gctcgcttca gattgttgca   120
aggctcaaga gcaacagcaa gcaagtgtgc attgatccca gctaaagtg gatccaggaa   180
tatctggaga aagctttaaa caaggaagct gcggcaaaag aggcagctgc gaaggaagcg   240
gcagcgaaag catctctatc atcagcgaaa aggaaacctc ttcaaacatt aataaaggat   300
ttagaaatat tggaaaatat caagaacaag attcatctcg agctctacac accaactgag   360
acccaggagt gcacccagca aactctgcag tgttacctgg gagaagtggt tactctgaag   420
aaagaaactg aagatgacac tgaaattaaa gaagaatttg taactgctat tcaaaatatc   480
gaaaagaacc tcaagagtct tacgggtcta aatcacaccg aagtgaatg caagatctgt   540
gaagctaaca caagaaaaa atttcctgat tttctccatg aactgaccaa ctttgtgaga   600
tatctgcaaa aataa                                                   615
```

```
<210> SEQ ID NO 44
<211> LENGTH: 204
<212> TYPE: PRT
<213> ORGANISM: Artificial Sequence
<220> FEATURE:
<223> OTHER INFORMATION: Amino acid sequence of fusion protein

<400> SEQUENCE: 44

Lys Pro Val Ser Leu Thr Tyr Arg Cys Pro Cys Arg Phe Phe Glu Ser
1               5                   10                  15
Asn Val Ala Arg Ala Asn Ile Lys His Leu Lys Ile Leu Ser Thr Pro
            20                  25                  30
Asn Cys Ser Leu Gln Ile Val Ala Arg Leu Lys Ser Asn Ser Lys Gln
        35                  40                  45
Val Cys Ile Asp Pro Lys Leu Lys Trp Ile Gln Glu Tyr Leu Glu Lys
    50                  55                  60
Ala Leu Asn Lys Glu Ala Ala Lys Glu Ala Ala Lys Glu Ala
65                  70                  75                  80
Ala Lys Ala Ser Leu Ser Ser Ala Lys Arg Lys Pro Leu Gln Thr
            85                  90                  95
Leu Ile Lys Asp Leu Glu Ile Leu Glu Asn Ile Lys Asn Lys Ile His
            100                 105                 110
Leu Glu Leu Tyr Thr Pro Thr Glu Thr Gln Glu Cys Thr Gln Gln Thr
        115                 120                 125
Leu Gln Cys Tyr Leu Gly Glu Val Val Thr Leu Lys Lys Glu Thr Glu
    130                 135                 140
```

Asp Asp Thr Glu Ile Lys Glu Glu Phe Val Thr Ala Ile Gln Asn Ile
145                 150                 155                 160

Glu Lys Asn Leu Lys Ser Leu Thr Gly Leu Asn His Thr Gly Ser Glu
            165                 170                 175

Cys Lys Ile Cys Glu Ala Asn Asn Lys Lys Phe Pro Asp Phe Leu
        180                 185                 190

His Glu Leu Thr Asn Phe Val Arg Tyr Leu Gln Lys
        195                 200

<210> SEQ ID NO 45
<211> LENGTH: 933
<212> TYPE: DNA
<213> ORGANISM: Artificial Sequence
<220> FEATURE:
<223> OTHER INFORMATION: Nucleotide sequence of fusion protein

<400> SEQUENCE: 45
aagcctgtca gcctgactta ccgatgcccc tgtcgattct tcgagagcaa cgtggcgagg    60
gccaacatta agcacctcaa aatcctttcc actcccaact gctcgcttca gattgttgca   120
aggctcaaga gcaacagcaa gcaagtgtgc attgatccca agctaaagtg gatccaggaa   180
tatctggaga aagctttaaa caaggaagct gcggcaaaag aggcagctgc gaaggaagcg   240
gcagcgaaac acatgaagat ggataagatg gaagaggtgt tgagttttaaa tgaagattac   300
atctttctga aaaagtgca gaaatgtcag acggagaag atcagaagtc gacattattg   360
gactgtgaaa agttctaaa ggcttccag acctccaat gcagggatag acagccagt    420
gaggagttgc caaaatttga atgcacaga ggtcatgagc accccccactt gaagagtagg   480
aatgagacat ctgtggcaga ggagaagagg cagccgatcg caacacacct ggcaggggtg   540
aagagcaaca acagtgag agtgctgaag tggatgacga cgggctacgc cccaacgagc   600
agcttgatat cctaccatga ggggaagctg aaggtggaga agcagggct ctactacatc   660
tactcacaag tcagcttctg caccaaggcg gcggcttcgg cgccattcac cctctatatt   720
tatttgtacc tcccccatgga agaggaccgg ctcctgatga agggacttga cacgcacagc   780
acctccacgg ctctctgtga gctccagtcc atccgggagg gcggtgtctt cgagctgcgg   840
cagggcgaca tggactttgt caatgtgacg gactcaacag cagtgaacgt caaccctggc   900
aacacctact ttggcatgtt caagctgtag taa                                 933

<210> SEQ ID NO 46
<211> LENGTH: 309
<212> TYPE: PRT
<213> ORGANISM: Artificial Sequence
<220> FEATURE:
<223> OTHER INFORMATION: Amino acid sequence of fusion protein

<400> SEQUENCE: 46

Lys Pro Val Ser Leu Thr Tyr Arg Cys Pro Cys Arg Phe Phe Glu Ser
1               5                   10                  15

Asn Val Ala Arg Ala Asn Ile Lys His Leu Lys Ile Leu Ser Thr Pro
            20                  25                  30

Asn Cys Ser Leu Gln Ile Val Ala Arg Leu Lys Ser Asn Ser Lys Gln
        35                  40                  45

Val Cys Ile Asp Pro Lys Leu Lys Trp Ile Gln Glu Tyr Leu Glu Lys
    50                  55                  60

Ala Leu Asn Lys Glu Ala Ala Ala Lys Glu Ala Ala Ala Lys Glu Ala
65                  70                  75                  80

```
Ala Ala Lys His Met Lys Met Asp Lys Met Glu Glu Val Leu Ser Leu
            85                  90                  95

Asn Glu Asp Tyr Ile Phe Leu Arg Lys Val Gln Lys Cys Gln Thr Gly
            100                 105                 110

Glu Asp Gln Lys Ser Thr Leu Leu Asp Cys Glu Lys Val Leu Lys Gly
            115                 120                 125

Phe Gln Asp Leu Gln Cys Arg Asp Arg Thr Ala Ser Glu Glu Leu Pro
            130                 135                 140

Lys Phe Glu Met His Arg Gly His Glu His Pro His Leu Lys Ser Arg
145                 150                 155                 160

Asn Glu Thr Ser Val Ala Glu Glu Lys Arg Gln Pro Ile Ala Thr His
                165                 170                 175

Leu Ala Gly Val Lys Ser Asn Thr Thr Val Arg Val Leu Lys Trp Met
            180                 185                 190

Thr Thr Ser Tyr Ala Pro Thr Ser Ser Leu Ile Ser Tyr His Glu Gly
            195                 200                 205

Lys Leu Lys Val Glu Lys Ala Gly Leu Tyr Tyr Ile Tyr Ser Gln Val
            210                 215                 220

Ser Phe Arg Thr Lys Ala Ala Ser Ala Pro Phe Thr Leu Tyr Ile
225                 230                 235                 240

Tyr Leu Tyr Leu Pro Met Glu Glu Asp Arg Leu Leu Met Lys Gly Leu
                245                 250                 255

Asp Thr His Ser Ala Ser Thr Ala Leu Cys Glu Leu Gln Ser Ile Arg
            260                 265                 270

Glu Gly Gly Val Phe Glu Leu Arg Gln Gly Asp Met Val Phe Val Asn
            275                 280                 285

Val Thr Asp Ser Thr Ala Val Asn Val Asn Pro Gly Asn Thr Tyr Phe
            290                 295                 300

Gly Met Phe Lys Leu
305

<210> SEQ ID NO 47
<211> LENGTH: 666
<212> TYPE: DNA
<213> ORGANISM: Artificial Sequence
<220> FEATURE:
<223> OTHER INFORMATION: Nucleotide sequence of fusion protein

<400> SEQUENCE: 47
aagcctgtca gcctgactta ccgatgcccc tgtcgattct tcgagagcaa cgtggcgagg      60
gccaacatta gcacctcaa aatcctttcc actcccaact gctcgcttca gattgttgca     120
aggctcaaga gcaacagcaa gcaagtgtgc attgatccca agctaaagtg gatccaggaa     180
tatctggaga aagctttaaa caaggaagct gcggcaaaag aggcagctgc gaaggaagcg     240
gcagcgaaaa tcgcaacaca cctggcaggg gtgaagagca cacaacagt gagagtgctg     300 aagtggatga cgacgggcta cgccccaacg agcagcttga tatcctacca tgaggggaag     360
ctgaaggtgg agaaagcagg gctctactac atctactcac aagtcagctt ctgcaccaag     420
gcggcggctt cggcgccatt caccctctat atttatttgt acctcccat ggaagaggac      480 cggctcctga tgaagggact tgacacgcac agcacctcca cggctctctg tgagctccag     540
tccatccggg agggcggtgt cttcgagctg cggcagggcg acatggactt tgtcaatgtg     600
acggactcaa cagcagtgaa cgtcaaccct ggcaacacct actttggcat gttcaagctg     660
tagtaa                                                               666
```

```
<210> SEQ ID NO 48
<211> LENGTH: 220
<212> TYPE: PRT
<213> ORGANISM: Artificial Sequence
<220> FEATURE:
<223> OTHER INFORMATION: Amino acid sequence of fusion protein

<400> SEQUENCE: 48

Lys Pro Val Ser Leu Thr Tyr Arg Cys Pro Cys Arg Phe Phe Glu Ser
1               5                   10                  15

Asn Val Ala Arg Ala Asn Ile Lys His Leu Lys Ile Leu Ser Thr Pro
            20                  25                  30

Asn Cys Ser Leu Gln Ile Val Ala Arg Leu Lys Ser Asn Ser Lys Gln
        35                  40                  45

Val Cys Ile Asp Pro Lys Leu Lys Trp Ile Gln Glu Tyr Leu Glu Lys
    50                  55                  60

Ala Leu Asn Lys Glu Ala Ala Lys Glu Ala Ala Lys Glu Ala
65                  70                  75                  80

Ala Ala Lys Ile Ala Thr His Leu Ala Gly Val Lys Ser Asn Thr Thr
                85                  90                  95

Val Arg Val Leu Lys Trp Met Thr Thr Ser Tyr Ala Pro Thr Ser Ser
            100                 105                 110

Leu Ile Ser Tyr His Glu Gly Lys Leu Lys Val Glu Lys Ala Gly Leu
        115                 120                 125

Tyr Tyr Ile Tyr Ser Gln Val Ser Phe Arg Thr Lys Ala Ala Ala Ser
    130                 135                 140

Ala Pro Phe Thr Leu Tyr Ile Tyr Leu Tyr Leu Pro Met Glu Glu Asp
145                 150                 155                 160

Arg Leu Leu Met Lys Gly Leu Asp Thr His Ser Ala Ser Thr Ala Leu
                165                 170                 175

Cys Glu Leu Gln Ser Ile Arg Glu Gly Gly Val Phe Glu Leu Arg Gln
            180                 185                 190

Gly Asp Met Val Phe Val Asn Val Thr Asp Ser Thr Ala Val Asn Val
        195                 200                 205

Asn Pro Gly Asn Thr Tyr Phe Gly Met Phe Lys Leu
    210                 215                 220
```

CHEMOKINE-CYTOKINE FUSION PROTEINS OF SDF-1 AND CD40L

CROSS-REFERENCE TO RELATED APPLICATIONS

This application is a Continuation of copending U.S. application Ser. No. 14/649,714, filed on Jun. 4, 2015, which is the National Phase under 35 U.S.C. § 371 of International Application No. PCT/CN2012/001629, filed on Dec. 5, 2012, all of which are hereby expressly incorporated by reference into the present application.

FIELD OF THE INVENTION

The present invention relates to fusion protein, comprising a chemokine and a cytokine connected thereto, wherein the chemokine and the cytokine have a mutual target cell, and the fusion protein has an improved cytokine activity and an improved chemokine activity.

BACKGROUND OF THE INVENTION

Cytokines are a group of proteins that cells release upon excitation (only very few cytokines are expressed on cell membranes). Cytokines produced by cells can affect target cells nearby or through blood circulation at very low concentration. They have broad functions on promoting growth, differentiation and activation of target cells. Many cytokines can target immune cells and play a role in immune response. Based on structural and functional differences, cytokines may be broadly divided into chemokines, interleukins, growth factors, transforming growth factors, colony stimulating factors, tumor necrosis factors, and interferons, etc.

Chemokines are a group of cytokines being able to attract leukocytes, which are generally positively charged, secretory proteins having small molecule weights. Their main function is to attract immune cells to a region having tissue injuries or pathogen infection, allowing leukocytes to subsequently perform phagocytosis or elicit inflammation against pathogens at this specific site. Leukocytes attracted by chemokines may include neutrophils, monocytes/macrophages, natural killer cells, dendritic cells and other leukocytes, which are of innate immunity; and T lymphocytes (T cells) or B lymphocytes (B cells) of adaptive immunity. Accordingly, chemokines play a very important role in the immune system of living organisms. Most chemokines have four highly conserved cysteine (C) forming disulfide bonds to stable their structure. Based on different numbers of amino acids between the first two Cs and the procession of the first C or not, they may be classified into four subfamilies of CXC (or α), CC (or β), C (or γ) and $CX_3C$. Stromal cell-derived factor-1 (SDF-1) is classified into the CXC subfamily of chemokines, and is also known as CXC ligand 12 (CXCL12). Having been observed in many species including humans, mice and cats of mammals and *Xenopus* of amphibians, and zebra fishes, it has little variation between different species and is highly conserved (Shirozu et al., *Genomics* 28, 495-500). mRNAs transcribed from SDF-1 gene in mice and humans are subject to different splicings and thus two isoforms of SDF-1 may be observed: SDF-1α and SDF-1β. The distribution of SDF-1 is very wide, and can be detected, including in lymphoid tissue, kidney, lung, liver, brain and muscle (Shirozu et al., *Genomics* 28, 495-500). SDF-1 receptor CXCR4 not only constantly presents in organs, but can also be seen in hematopoietic stem cells, endothelial cells, dendritic cells, B cells and T cells. Therefore, these cells are attracted by SDF-1 to migrate to the site with high concentration of the chemokines (Bleul et al., *Nature,* 382: 829-833; Oberlin et al., *Nature* 382: 833-835; Read et al., *Developmental and comparative immunology,* 29, 143-152). Interleukin-8 (IL-8) is also classified into the CXC subfamily of chemokines (also known as CXCL8). After initial discovery in humans, it was successively observed in economic animals of pigs, cows and chickens. IL-8 at low concentration is able to attract several immune cells, including monocytes, macrophages, lymphocytes, neutrophils, etc.

CD40 ligand (CD40L) is a member of tumor necrosis factor (TNF) superfamily, which is a cytokine having functions on tumor necrosis and promoting differentiation, proliferation and apoptosis of white blood cells. CD40L is synthesized as a transmembrane protein. Take human CD40L as an example, the protein has a total of 261 amino acids, with first 22 amino-terminal amino acids being intracellular region, followed by 24 amino acids being transmembrane region, and 215 carboxy-terminal amino acids being extracellular (Exc) region, wherein the Exc region has at its carboxy terminus a TNF homology (TNFh) region conserved for all TNF superfamily proteins. CD40L presents mainly in the form of a transmembrane protein on the surface of activated $CD4^+$ T cells, and also presents on $CD8^+$ T cells, basophils, eosinophils, mast cells, natural killer cells, platelets, and even on the surface of CD40-expressing cells.

CD40, receptor of CD40L, is distributed on the surfaces of antigen presenting cells (APCs) of B cells, dendritic cells, macrophages, etc. Physiologically, these antigen presenting cells can be activated by CD40L expressed by T helper cells, promoting the expression of major histocompatibility complex class II (MHC-II) molecules and B7 molecules to assist in antigen presentation. CD40L activates signal transduction pathways by binding to CD40 on target cells. In addition to the aforementioned promotion of antigen presentation, effecting on B cells, CD40L can promote B cell proliferation, isotype switching of immunoglobulins, antibody secretion, memory B cell differentiation, or prevention of apoptosis; effecting on macrophages, CD40L can enhance their activation, production of interleukin-12 (IL-12) to activate T helper 1 (Th1), or secretion of chemokines, or the production of nitric oxide (NO) to promote microorganism defense ability of macrophages; effecting on dendritic cells, it can make them mature and activated, wherein the mature dendritic cells not only express a large amount of MHC-II molecules to promote antigen presentation, but also secrete chemokines of TNF-α and IL-8, macrophage inflammatory protein 1a (MIP-1a), etc.

There are many researches that apply CD40L on vaccine adjuvant or treatment, for example, as adjuvants for duck hepatitis B virus (DHBV) vaccines (Gares et al., *Clin Vaccine Immunol* 13, 958-965), human immunodeficiency virus (HIV) DNA vaccines (Stone et al., *J Virol* 80, 1762-1772), or in the treatment of human autoimmune diseases (Howard & Miller, *Autoimmunity* 37, 411-418), etc.

IL-2 is classified into the hematopoietin family, the family including a number of cell growth-related hormones or other cytokines, etc. Functions of IL-2 include: regulating the maturation and differentiation of T cells, stimulating proliferation and antibody secretion of B cells, promoting cytotoxicity of natural killer cells, and activating monocytes and macrophages, etc. IL-2 can also stimulate T cells and B cells to continue expressing MHC, and also stimulate natural killer cells to produce several different cytokines, including TNF-α, IFN-γ and granulocyte/macrophage colony stimulating factor (GM-CSF), etc. Studies have shown that IL-2 has anti-tumor and vaccine-enhancing effects.

However, there remains a need in the art for cytokines and chemokines with an improved activity.

BRIEF SUMMARY OF THE INVENTION

It was unexpectedly found in the present invention that a fusion protein comprising a chemokine and a cytokine connected to the chemokine has an improved cytokine activity and an improved chemokine activity.

Accordingly, the present invention provides a fusion protein, comprising a chemokine polypeptide, which a chemokine or a receptor binding domain thereof; and a cytokine polypeptide connected to the chemokine polypeptide, which is an interleukin, a TNF-superfamily cytokine, or a receptor binding domain thereof; wherein the chemokine polypeptide and the cytokine polypeptide have a common target cells, and the fusion protein has an improved chemokine activity as compared to the chemokine polypeptide, and an improved cytokine activity as compared to the cytokine polypeptide.

According to the present invention, the chemokine is a CXC chemokine, CC chemokine, C chemokine, and chemokine $CX_3C$, preferably CXC chemokine. According to one embodiment of the present invention, the chemokine may be a stromal cell derived factor (SDF-1) or IL-8.

According to the present invention, the cytokine polypeptide is an interleukin, a TNF-superfamily cytokine, or a receptor binding domain thereof. In one embodiment of the present invention, the cytokine polypeptide is IL-2, CD40 ligand, or a receptor binding domain thereof.

In another aspect, the present invention provides an isolated nucleic acid molecule, which encodes a fusion protein of the present invention.

In yet another aspect, the present invention provides an expression vector, comprising a nucleic acid molecule of the invention.

The present invention also provides a host cell, comprising an expression vector of the invention or a nucleic acid molecule of the invention.

Details of various embodiments of the present invention are described below. Other features of the invention will be apparent from the detailed description of various embodiments and the claims.

Without further elaboration, it is believed that a person of ordinary skill in the art to which the present invention belongs can utilize the invention to its broadest extent based on the description above. It is to be understood that the following detailed description are exemplary and are not restrictive of the other disclosure in any way.

BRIEF DESCRIPTION OF THE DRAWINGS

The foregoing summary, as well as the following detailed description of the invention, will be better understood when read in conjunction with the appended drawing. In the drawings.

DETAILED DESCRIPTION OF THE INVENTION

Figure 1:
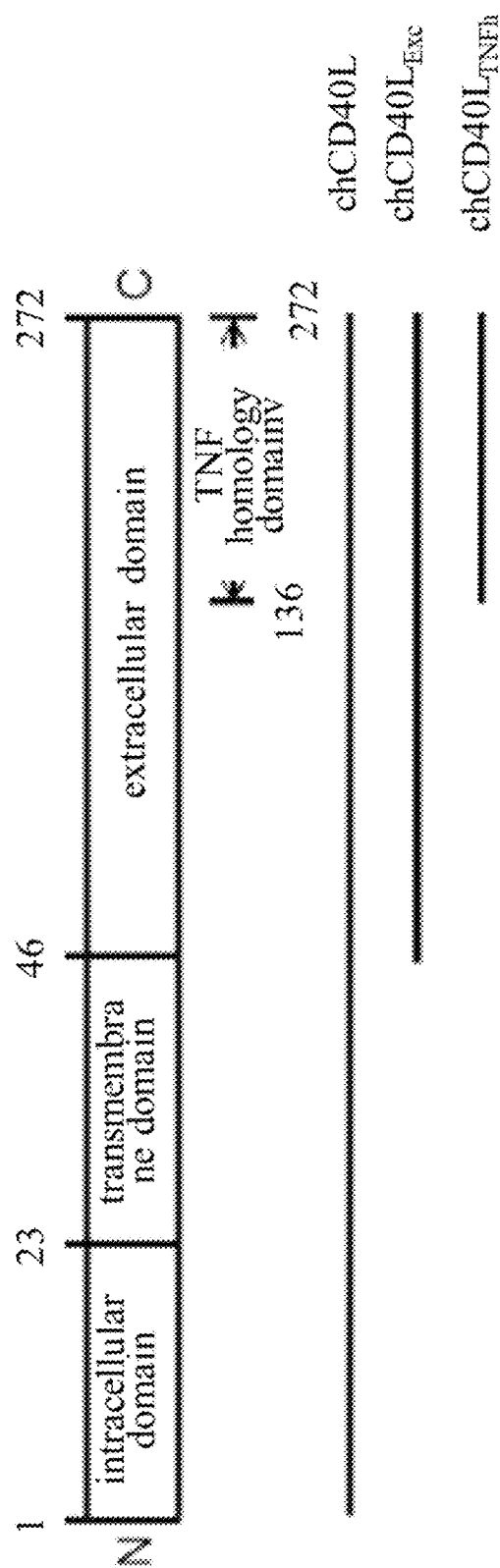
FIG. 1 is a schematic diagram for chicken CD40L and its derivative proteins, $CD40L_{Exc}$ and $CD40L_{TNFh}$.

Unless defined otherwise, all technical and scientific terms used herein have the same meaning as commonly understood by a person skilled in the art to which this invention belongs.

As used herein, the singular forms "a", "an", and "the" refer to one or more referents unless the context clearly dictates otherwise.

The term "chemokine polypeptide" as used herein refers to a polypeptide, which is a chemokine or a receptor binding domain thereof, wherein the chemokine includes but is not limited to CXC chemokines, CC chemokines, C chemokines and $CX_3C$ chemokines.

The term "cytokine polypeptide" as used herein refers to a polypeptide, which is a cytokine or a receptor binding domain thereof, wherein the cytokine includes but is not limited to interleukins and cytokines of TNF-superfamily.

The term "chemokine activity" as used herein refers to the activities which chemokines possess or are able to exert in vivo, including but not limited to, chemotaxis of a variety of immune cells (including monocytes, macrophages, T cells, B cells, natural killer cells, dendritic cells and neutrophils, etc.).

The term "cytokine activity" as used herein refers to the activities which cytokines possess or are able to exert in vivo, including but not limited to the promotion of proliferation, immunoglobulin class switching and antibody secretion of B cells; differentiation of memory B cells, or prevention of their apoptosis; promoting macrophages' secretion of interleukin-12 to activate type I helper T cells or secrete chemokines; promoting macrophages to produce nitric oxide to enhance the defense capability against microorganisms; promoting the maturation and activation of dendritic cells; regulation of the maturation and differentiation of T cells; promoting the cytotoxicity and the production of a variety of different cytokines of natural killer cells; activation of monocytes and macrophages; and stimulation of T cells and B cells to continuously express MHC, etc.

The present invention provides a fusion protein, comprising a chemokine polypeptide, which is a chemokine or a receptor binding domain thereof, and a cytokine polypeptide connected to the chemokine polypeptide, which is a interleukin, a TNF-superfamily cytokine or a receptor binding domain thereof; wherein the chemokine polypeptide and the cytokine polypeptide have a common target cell, and the fusion protein has an improved chemokine activity as compared to the chemokine polypeptide, and an improved cytokine activity as compared to the cytokine polypeptide.

In preferred embodiments of the present invention, the chemokine polypeptide and the cytokine polypeptide are connected by a peptide linker. To join two proteins together and retain their original configurations and functions, an appropriate peptide linker may be added between the two proteins to reduce the interference with each other when the proteins fold. And such peptide linker may be a flexible peptide linker (Gly-Gly-Gly-Gly-Ser)$_n$ (usually n is less than 6) with a certain extent of flexibility and hydrophilicity, or a hydrophilic helical peptide linker (Glu-Ala-Ala-Ala-Lys)$_n$ (usually n is less than 6).

In one embodiment of the invention, the chemokine is a CXC chemokine. In a certain embodiment, the chemokine is stromal cell-derived factor is (SDF-1). In another certain embodiment, the chemokine is IL-8.

In certain embodiments of the present invention, the chemokine polypeptide has an amino acid sequence selected from the following: SEQ ID NO: 2, 4, 6, 8, 10, 12, 14, 16, 18, and a homolog thereof and an analog thereof.

In certain embodiments of the present invention, the cytokine is IL-2, CD40 ligand (CD40L) or a receptor binding domain thereof.

In certain embodiments of the present invention, the cytokine polypeptide has an amino acid sequence selected from the following: SEQ ID NO: 20, 22, 24, 26, 28, 30, 32, 34, 36, 38, and a homolog thereof and an analog thereof.

In certain embodiments of the present invention, the fusion protein of the present invention has an amino acid sequence selected from the following: SEQ ID NO: 40, 42, 44, 46 and 48.

In another aspect, the present invention provides an isolated nucleic acid molecule, which encodes a fusion protein of the present invention.

In certain embodiments of the present invention, the isolated nucleic acid molecule comprises a nucleotide sequence encoding a chemokine polypeptide, selected from the following: SEQ ID NO: 1, 3, 5, 7, 9, 11, 13, 15, 17, and a homolog thereof and an analog thereof.

In certain embodiments of the invention, the isolated nucleic acid molecule comprises a nucleotide sequence encoding a chemokine polypeptide, selected from the following: SEQ ID NO: 19, 21, 23, 25, 27, 29, 31, 33, 35, 37, and a homolog thereof and an analog thereof.

In certain embodiments of the invention, the isolated nucleic acid molecule has a sequence of one selected from the following: SEQ ID NO: 39, 41, 43, 45 and 47.

In yet another aspect, the present invention provides an expression vector, comprising a nucleic acid molecule of the invention.

The present invention also provides a host cell comprising an expression vector of the invention or a nucleic acid molecule of the invention.

The following examples are merely illustrative and not restrictive to the present invention.

EXAMPLE 1

Construction of Prokaryotic Expression Vectors

Previously constructed expression vectors for chicken SDF-1, IL-8, CD40L derivative proteins and IL-2 (Pei-Shan Wu, National Chung Hsing University, Institute of Veterinary Microbiology, 2008 Master's thesis, Studies on chicken CD40L and chemokines; Tsai et al., *Taiwan Vet J* 31: 38-45) were used as a template for recombinant polymerase chain reactions, wherein the chicken CD40L (chCD40L) derivative protein includes an extracellular domain of CD40L (CD40L$_{Exc}$) or TNF homology domain of CD40L (CD40L$_{Exc}$) (see FIG. 1). Genes sequences of conjugate proteins or fusion proteins SDF1CD40L$_{Exc}$, SDF1CD40L$_{TNFh}$, SDF1IL2, IL8CD40L$_{Exc}$, IL8CD40L$_{TNFh}$, IL8IL2, etc. were expanded therefrom.

The methods are briefly described as follows. Two specific primer pairs were designed based on the sequences of each of the genes. Forward primer of the first pair of primers has a gene sequence of an EcoR I restriction enzyme site and a front N-terminus of the fusion protein, and the reverse primer has a gene sequence of a helical peptide linker and a front C-terminus of the fusion protein. This pair of primers can specifically amplify DNA fragments encoding the front section of the fusion protein and the peptide linker. Forward primer of the second pair of primers has a gene sequence of a helical peptide linker and a rear N-terminus of the fusion protein, and the reverse primer has a gene sequence of a Xho I restriction enzyme site and a rear C-terminus of the fusion protein. This pair of primers can specifically amplify DNA fragments encoding the peptide linker and the rear section of the fusion protein. With the PCR products of this two primer pairs as templates, an additional PCR was performed using the forward primer of the first pair of primers and the reverse primer of the second pair of primers, and accordingly the two fragments were connected due to partial overlapping sequences of the helical peptide linker. The products obtained are fusion gene sequence comprising helical peptide linker gene therein.

After treating the above products with EcoR I and Xho I, a ligation with pET vectors (Novagen, Darmstad, Germany) treated by EcoR I and Xho I using T4 DNA ligase (Invitrogen) at 16° C. for 16 hour was performed. The constructed prokaryotic expression vector were respectively named as pETSDF1CD40L$_{Exc}$, pETSDF1CD40L$_{TNFh}$, pETSDF1IL2, pETIL8CD40L$_{Exc}$ and pETIL8IL2.

EXAMPLE 2

Expression of the Recombinant Proteins

The constructed prokaryotic expression vector was transformed into E. coli expression strain BL21 (DE3), 0.5 mM IPTG was used to induce the expression of the recombinant protein, and collected bacteria cells by centrifugation with the removal culture medium. Subsequently, all of bacteria cells were resuspended in binding buffer, a high pressure cell lysis instrument (French Pressure Cell Press, Thermo IEC, Needham, Height, Mass., USA) was used to lysis the bacteria cells, and soluble proteins located in the supernatant after high speed centrifugation were isolated using nickel ion affinity column.

Figure 2:
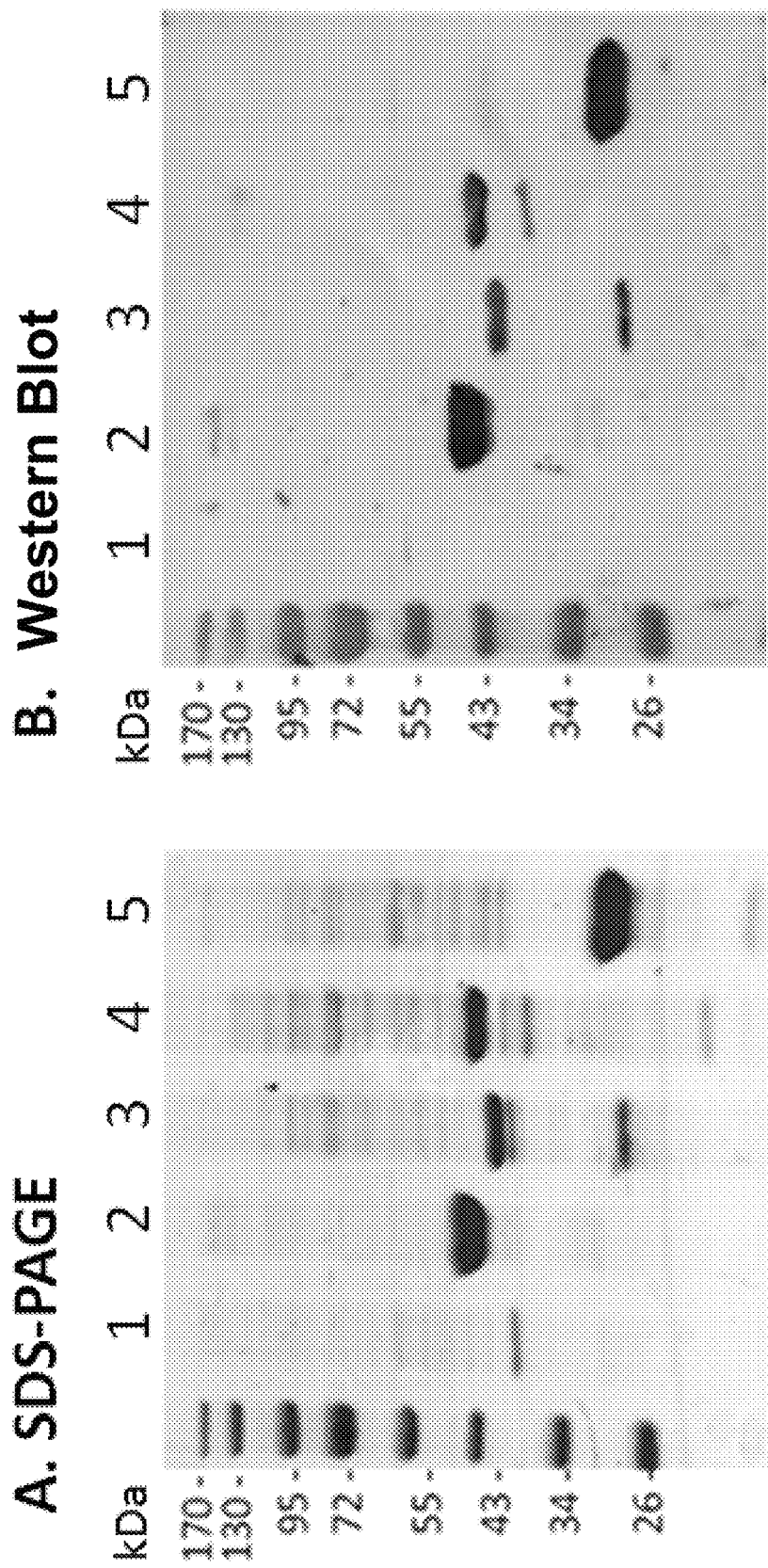
FIG. 2 shows the results of SDS-PAGE and western blot analysis of the expressed chicken recombinant proteins. Lane 1: $IL8CD40L_{Exc}$, expected size being 52 kDa; Lane 2: IL8IL2, expected size being 44 kDa; Lane 3: $SDF1CD40L_{Exc}$, expected size being 38 kDa; Lane 4: SDF1CD40LTNFh, expected size being 44 kDa; and Lane 5: SDF1IL2, expected size being 26 kDa.
Figure 3:
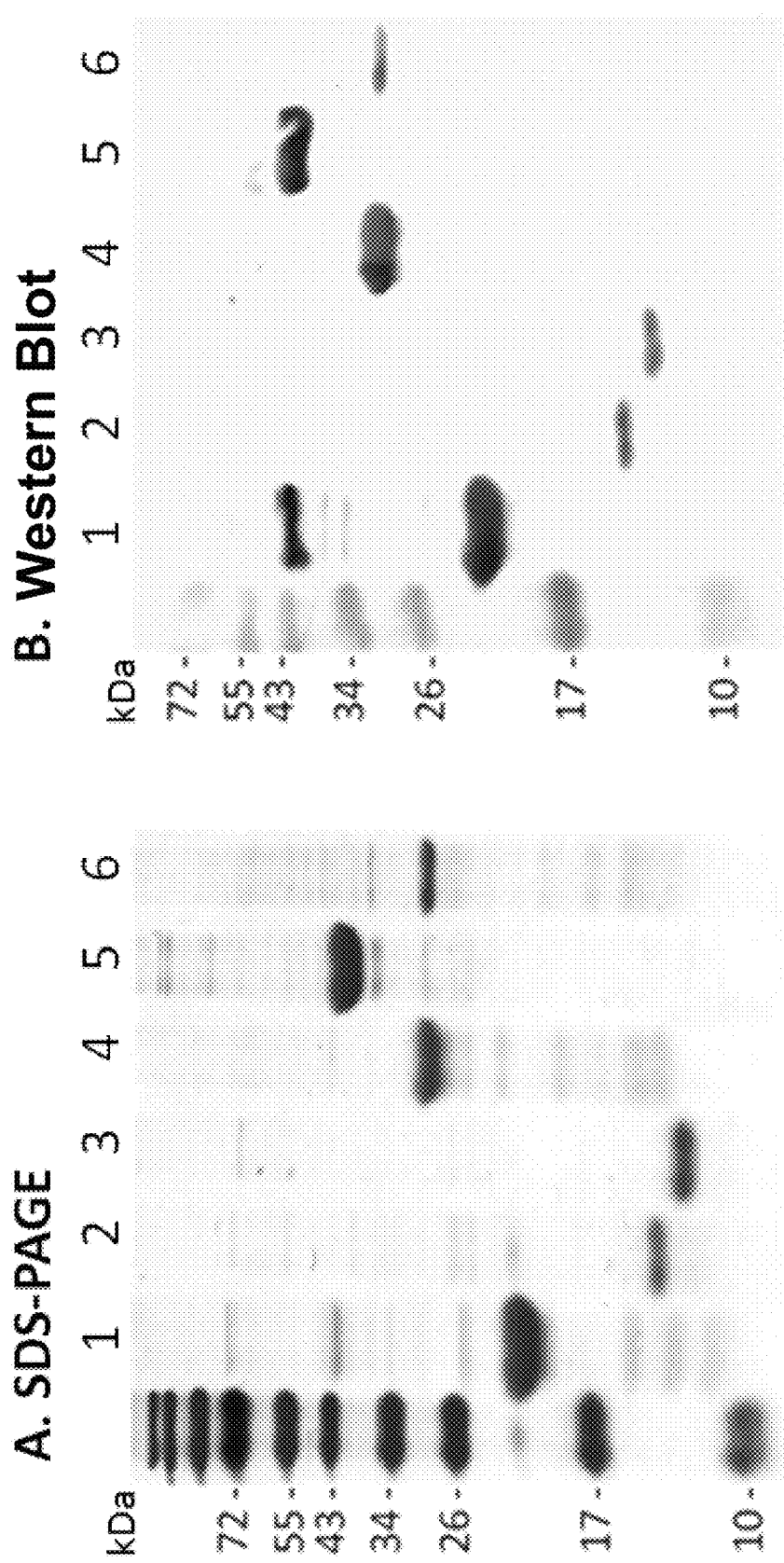
FIG. 3 shows the results of SDS-PAGE and western blot analysis for purified single proteins. Lane 1: tagged protein, expected size being 21 kDa; Lane 2: IL-8, expected size being 13 kDa; Lane 3: SDF-1, expected size being 11 kDa; Lane 4: IL-2, expected size being 32 kDa; Lane 5: $CD40L_{Exc}$, expected size being 42 kDa; and Lane 6: $CD40L_{TNFh}$, expected size being 33 kDa.

Insoluble protein located at the bottom pellet after centrifugation were treated with 8 M to unfold the proteins and they were dissolved in an aqueous solution, which was then subjected to a centrifugation of 12,000 rpm 30 minutes and dialysis of the supernatant was performed to slowly displace the urea, so that the proteins may refold to their original configurations. Lastly, the proteins were dissolved in phosphate buffer containing 10% glycerol (H 7.3), filtered through 0.22 μm membrane, concentration was determined by BCA protein assay kit (Pierce, Rockford, Ill., USA), and stored at −20° C. The isolated proteins were identified to be correct fusion proteins using MALDI-TOF mass spectrometer. SDS-PAGE and western blot (primary antibody being anti-His antibody, secondary antibody being AP- labeled goat anti-mouse IgG antibody, chromogenic reagent NBT/BCIP) analysis shows that the expressed chicken recombinant fusion proteins IL8CD40L$_{Exc}$, IL8IL2, SDF1CD40L$_{Exc}$, SDF1CD40L$_{TNFh}$ and SDF1IL2 etc. have the molecular weights as expected, respectively being 52 kDa, 44 kDa, 38 kDa, 44 kDa and 26 kDa (see FIG. 2). In addition, single proteins were also prepared and isolated as controls by the methods as described above (Pei-Shan Wu, National Chung Hsing University, Institute of Veterinary Microbiology, 2008 Master's thesis, Studies on chicken CD40L and chemokines; Tsai et al., Taiwan Vet J 31: 38-45).

EXAMPLE 3

Chemotactic Activity Assay

Chemotactic activities of chemokines (SDF-1, or IL-8) and CD40L derivative proteins or IL-2-fused chemokines were accessed. Peripheral blood mononuclear cells were isolated using Histopaque 1077 (Sigma, Saint Louis, Mo., USA), washed twice with PBS, suspended with 10% FBS in RPMI 1640 (Gibco, Grand Island, N.Y., USA), and then added into 0.6% liquid agar, mixed well, resulting in a final concentration of 0.3% of the agar. Subsequently, 2 μl/well of the mixture were dripped in the center of the wells on a 48-well plate, and placed in a refrigerator for five minutes to solidify the agar, thus fixing the cells within the agar. Each well was then added with 250 μl medium containing a respective concentration protein to be tested, cultured overnight before observation.

Figure 4:
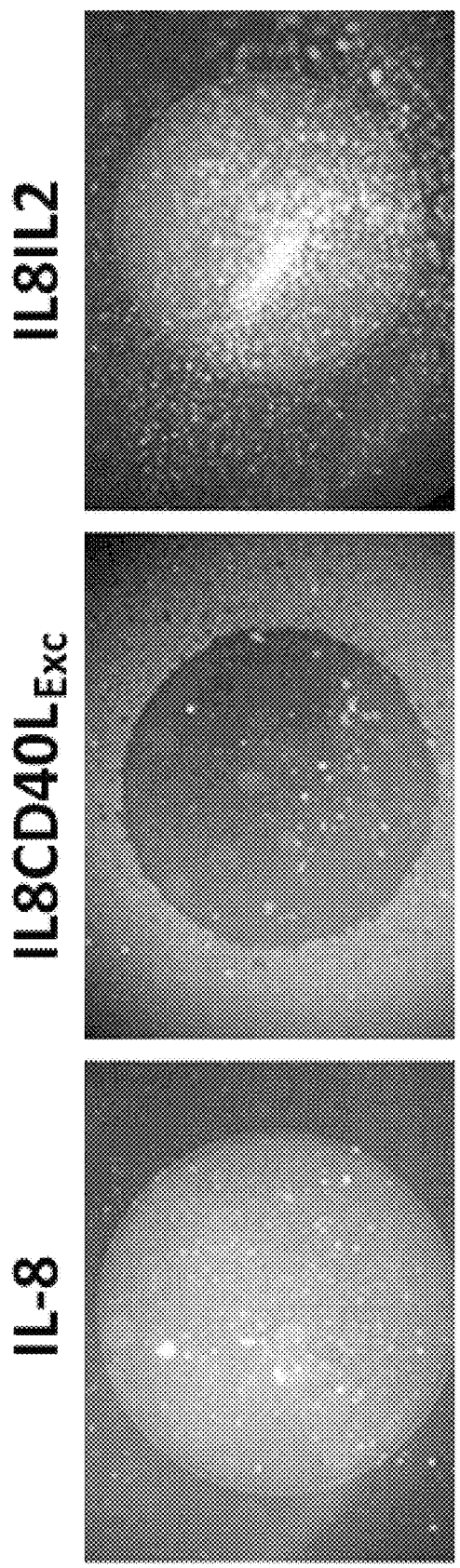
FIG. 4 shows the chemotaxis of PBMCs by IL-8 derivative proteins. Cells attracted by the chemokine outside the agar would travel from the center of the agar to the surrounding. Cells are seen cloudy at low magnification. More cells at the surrounding indicates greater degree of cell chemotaxis. At 2 μM, the chemotaxis extent of $IL8CD40L_{Exc}$ or IL8IL2 was significantly higher than single IL-8 protein.
Figure 5:
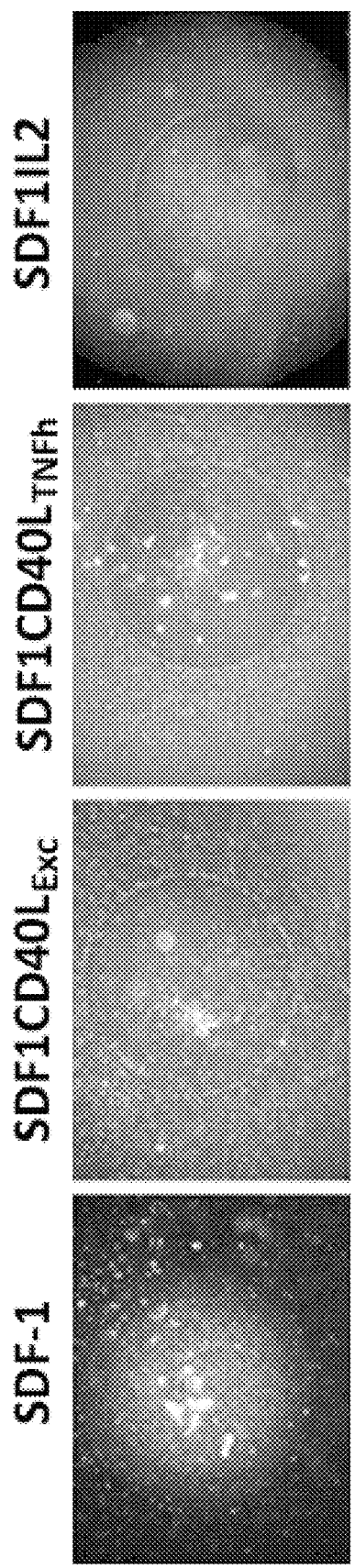
FIG. 5 shows the chemotaxis of PBMCs by SDF-1 derivative proteins. At 2 μM, the chemotaxis extent of $SDF1CD40L_{Exc}$, $SDF1CD40L_{TNFh}$, or SDF1IL2 was significantly higher than single SDF-1 protein.

Based on the minimum effective concentration (MEC) for each protein to exert chemotactic activity, with smaller MEC value indicating better chemotactic activity, IL-8 fused either with CD40L derivative protein or IL-2 (IL8CD40L$_{Exc}$ or IL8IL2) exhibited a smaller MEC value and a better chemotactic activity. The fusion proteins have a better chemotactic activity than IL-8 (see Table 1). SDF-1 fused either with CD40L derivative protein or IL-2 (SDF1CD40L$_{Exc}$ or SDF1IL2) exhibited a smaller MEC value and a better chemotactic activity. The fusion proteins have a better chemotactic activity than SDF-1 (see Table 1). The chemotactic effects are better in higher concentrations of proteins. At the same concentration, the chemotactic extent of IL8CD40L$_{Exc}$ (with the best chemotactic activity) or IL8IL2 (with the second best chemotactic activity) were clearly higher than single IL8 protein (see FIG. 4). And at the same concentration, the chemotactic extent of SDF1CD40L$_{Exc}$, SDF1CD40L$_{TNFh}$ or SDF1IL2 were clearly higher than simple mixture or single SDF-1 protein (see FIG. 5).

TABLE 1

Minimum effective concentrations (MECs) of chemotactic activity

| Group | Protein | MEC |
|---|---|---|
| A | IL-8 | 125 nM |
| B | IL8CD40L$_{Exc}$ | 62.5 nM |
| C | IL8IL2 | 62.5 nM |
| D | SDF-1 | 125 nM |
| E | SDF1CD40L$_{Exc}$ | 62.5 nM |
| F | SDF1CD40L$_{TNFh}$ | 62.5 nM |
| G | SDF1IL2 | 62.5 nM |

EXAMPLE 4

Analysis of Activation of Macrophages to Produce Nitric Oxide (NO) by CD40L Derivative Proteins Based on CD40L's property of being able to activate macrophages to produce NO, CD40L activities of a chemokine fused with a CD40L derivative protein were assessed. Peripheral blood mononuclear cells were isolated, washed twice with PBS, suspended in RPMI 1640 containing 10% FBS supplemented with 125 ng/ml chicken IL-2 and 4 μg/ml LPS at $2\times10^6$ cells/ml. One ml of cells were added to each well of a 24-well plates. One ml of fresh medium (also supplemented with 125 ng/ml chicken IL-2 and 4 μg/ml LPS) were added after 2 days. After 5 day simulation completed, monocytes differentiated into macrophages. After PBS washing 3 times to remove suspension cells, different concentrations of CD40L derivative proteins or fusion proteins were added, with the culture medium, tagged protein expressed by vectors and culture medium supplemented with 4 μg/ml LPS as negative and positive control groups. After 48 hour culture, 50 μl culture medium were taken and examined for nitrite (from NO) concentration using a commercially available kit (Griess Reagent System; Promega, Madison, Wis., USA).

Figure 6:
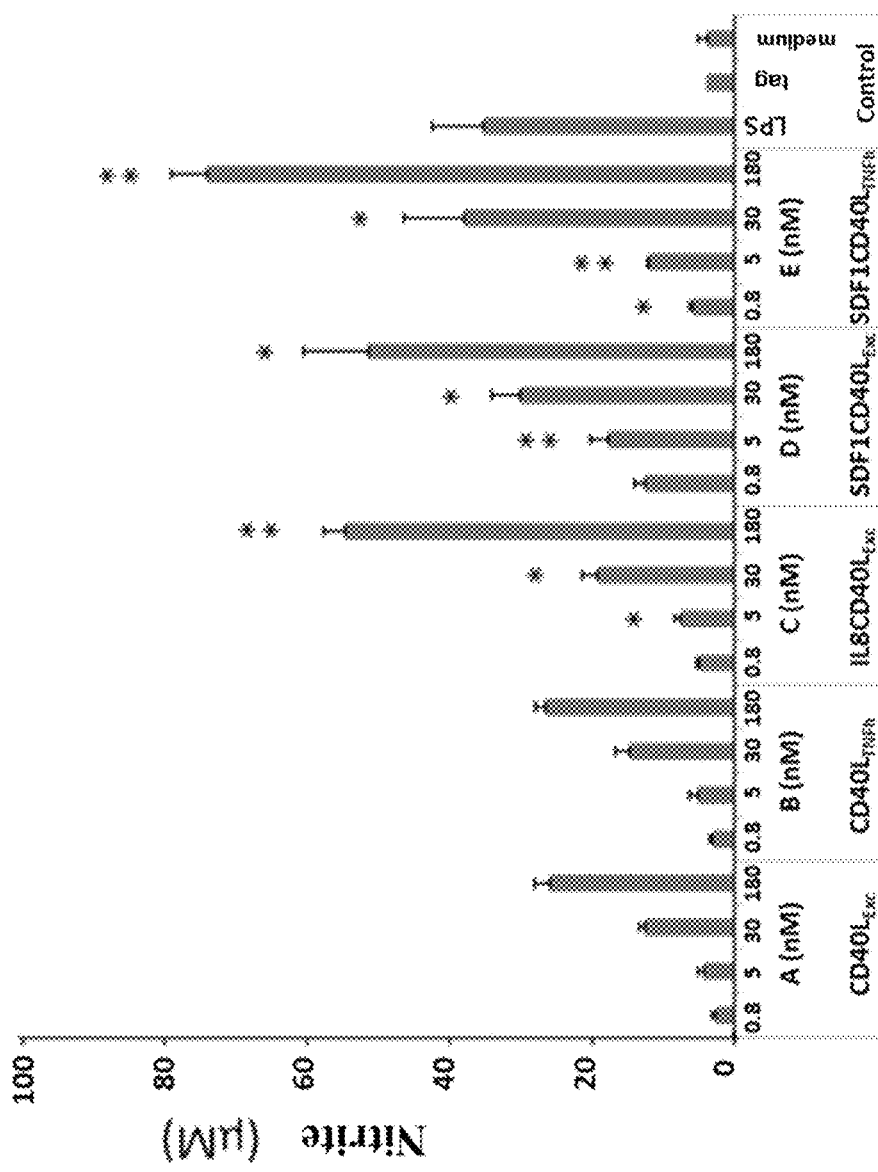
FIG. 6 shows the activities of CD40L derivative proteins on activating macrophages to produce NO. A: $CD40L_{Exc}$; B: $CD40L_{TNFh}$; C: $IL8CD40L_{Exc}$; D: $SDF1CD40L_{Exc}$; E: $SDF1CD40L_{TNFh}$; and the control group: LPS (4 μg/ml) as a positive control group, tagged protein (250 nM) and the culture medium as negative control groups. * represent significantly higher activity as compared to single proteins ($^*p<0.05$, $^{**}p<0.01$).

IL8CD40L$_{Exc}$ fusion protein exhibited a significantly better activity as compared to the group added CD40L$_{Exc}$ alone (5-30 nM, p<0.05; 180 nM, p<0.01). The effects of the fusion protein SDF1CD40L$_{Exc}$ were significantly better than CD40L$_{Exc}$ single protein (5 nM, p<0.01; 30-180 nM, p<0.05). For the combination of SDF-1 and CD40L$_{TNFh}$, similar results were obtained that SDF1CD40L$_{TNFh}$ fusion protein had a significantly better effects than a single CD40L$_{TNFh}$ protein (5 nM and 180 nM, p<0.01; 0.8 nM and 30 nM, p<0.05) (see FIG. 6).

EXAMPLE 5

Activity of IL2 Fusion Protein on Promoting Lymphocyte Proliferation

Figure 7:
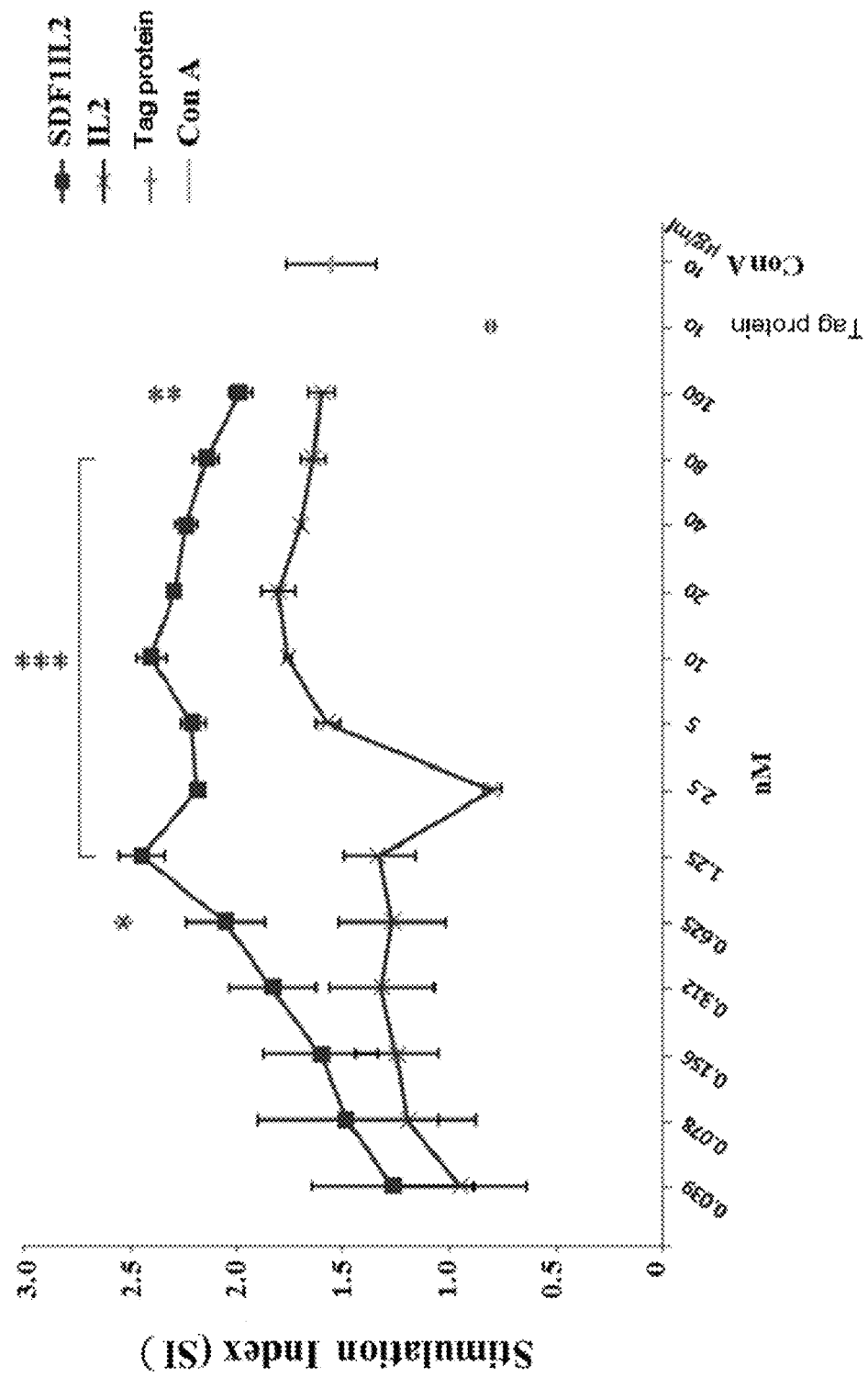
FIG. 7 shows the results of test on IL-2 fusion proteins' promotion of lymphocyte proliferation. Stimulation index (SI)=OD of test groups/OD of those cultured with RPMI 1640 only. At a concentration of 0.625-160 nM, the SI value of SDF1IL2 fusion protein was significantly higher than the IL-2 alone group ($^*p<0.05$, $^{}p<0.01$, $^{*}p<0.001$).

Based on the activity of IL2 on promoting lymphocyte proliferation, IL-2 activities of a chemokine fused with IL-2 were accessed. In view of that the activity of intracellular acid phosphatase are proportional to cell number, chromogenic substrate p-nitrophenyl phosphate (pNpp) was used. Peripheral blood mononuclear cells were isolated, and then cultured in RPMI 1640 containing 10% FBS supplemented with different concentrations of proteins, 10 μg/ml ConA (positive control group), or 10 nM tagged protein (negative control group) on 96-well plate at $2 \times 10^5$/well. After culture for 3 days, the culture was subjected to 3000 rpm centrifugation for 10 minutes, removed the culture medium, 100 μl chromogenic reagent (0.1 M sodium acetate, H 5.5, 0.1% Triton X-100, and 10 mM pNpp) were added to each well, and incubated at 37° C. for two hours. 10 μl 1 N NaOH were then added to terminate the reaction. Absorbance at a wavelength of 405 nm was read and used to calculate the stimulation index (SI), where SI=OD of experimental group/OD of RPMI 1640 culture only. The results show that at 0.625-160 nM SDF1IL2 fusion proteins exhibited significantly higher activity on proliferation promotion than IL-2 (0.625 nM, $p<0.05$; 1.25-80 nM, $p<0.001$; 160 nM, $p<0.01$). These results show that IL-2 activity was significantly improved after fused with a chemokine (see FIG. 7).

EXAMPLE 6

Figure 8:
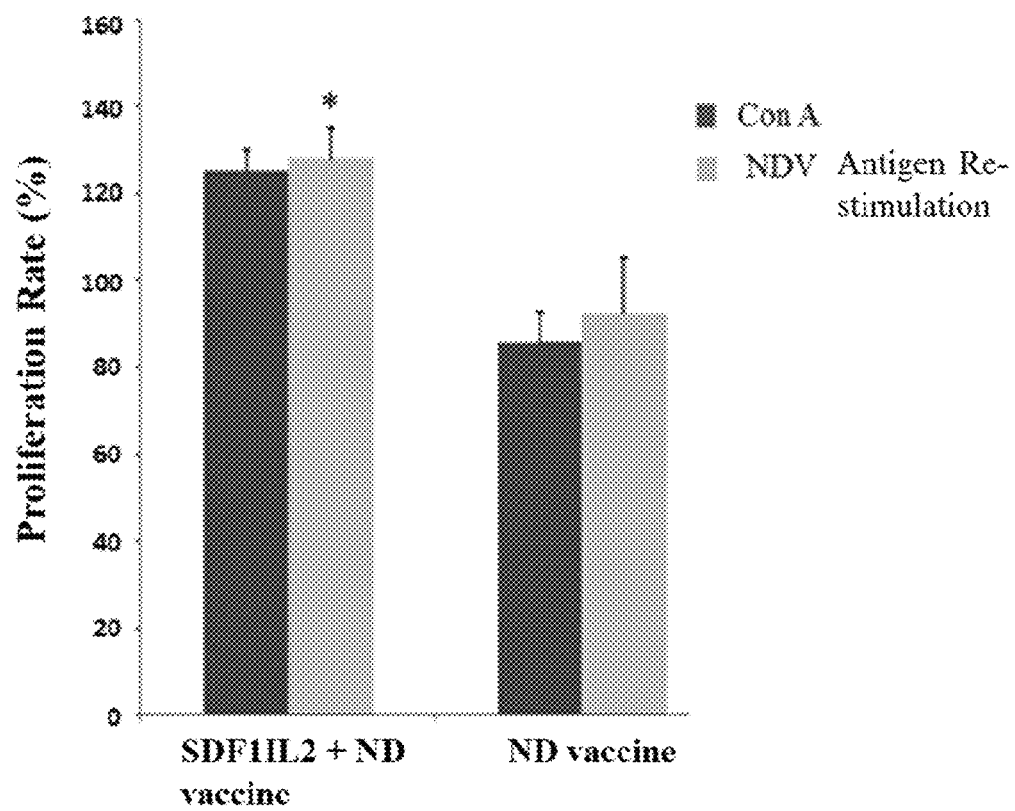
FIG. 8 shows that IL-2 fusion protein as an adjuvant of Newcastle disease (ND) vaccine can significantly promote cellular immune response. Chickens of the group administered with IL-2 fusion protein adjuvant and ND vaccine exhibited a significantly higher proliferation of memory lymphocytes upon Newcastle disease virus (NDV) antigen re-stimulation, as compared to the ND vaccine group.

Fusion Protein as Adjuvant of Newcastle Disease (ND) Vaccine Adjuvant to Promote Vaccine-Induced Immune Responses IL-2 fusion protein was used as an adjuvant of avian Newcastle disease (ND) vaccine and administered to chickens. After administration of the vaccine, the blood of the chickens was drawn for the culture of lymphocytes, and inactivated Newcastle disease virus (NDV) were added as antigen to perform antigen re-stimulation assay. 10 μg/ml ConA were added to the culture medium as the positive control group. The proliferation of memory lymphocytes that can recognize NDV antigen of each group of chickens was compared. The methods for determining proliferation state are the same as described in Example 5. Proliferation rate=(OD of test groups/OD of RPMI 1640 culture only)×100%. Compared with the group vaccinated with ND vaccine only, the groups vaccinated with IL-2 fusion proteins as ND vaccine adjuvant (SDF1IL2+ND vaccine) had a significantly enhanced proliferation of antigen-specific memory lymphocytes upon antigen re-stimulation (see FIG. 8).

EXAMPLE 7

Figure 9:
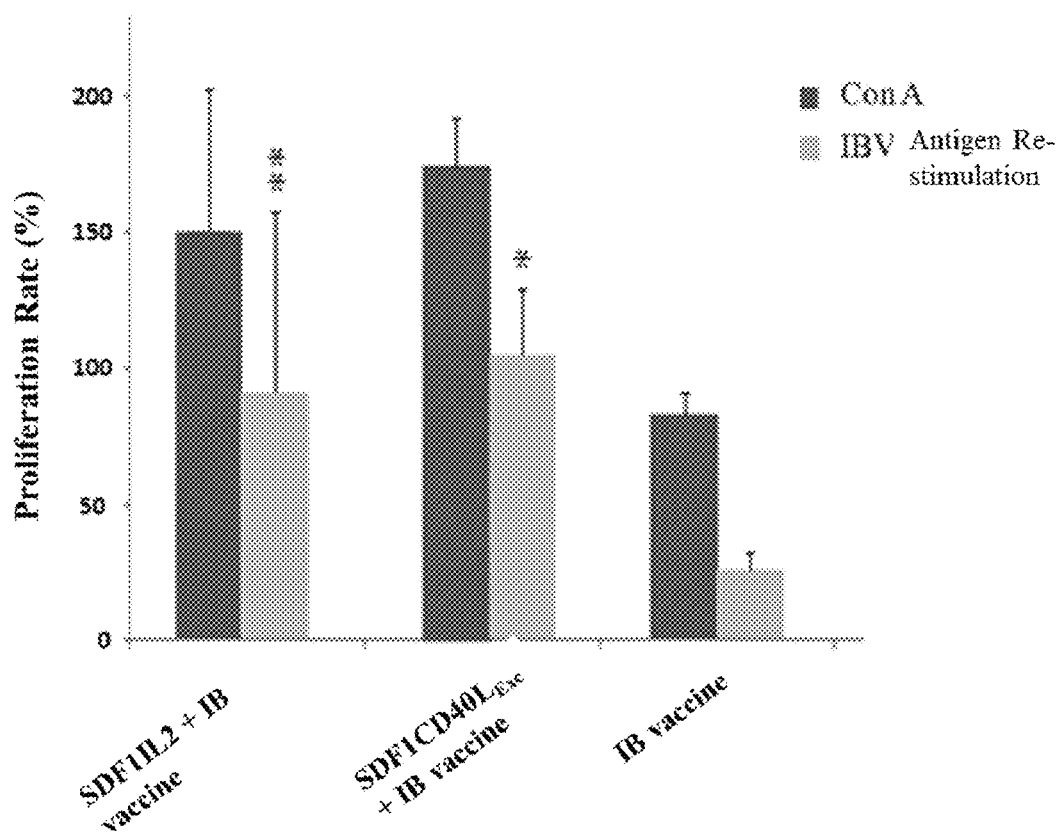
FIG. 9 shows that the fusion proteins as adjuvants of infectious bronchitis (IB) vaccine can significantly promote cellular immune response. Antigen re-stimulation tests were performed for infectious bronchitis virus (IBV). Chickens of the group administered with IL-2 fusion protein adjuvant and IB vaccine exhibited a significantly (p<0.01) higher proliferation of memory lymphocytes, as compared to the IB vaccine group. Chickens of the group administered with $CD40L_{Exc}$ fusion protein adjuvant and IB vaccine exhibited a significantly (p<0.05) higher proliferation of memory lymphocytes, as compared to the IB vaccine group.

Fusion Protein as Adjuvant of Avian Infectious Bronchitis (IB) Vaccine to Promote Vaccine-Induced Immune Responses IL-2 fusion proteins or $CD40L_{Exc}$ fusion proteins were used as an adjuvant of avian infectious bronchitis (IB) vaccine. After administration of the vaccine, the blood of the chickens was drawn for the culture of lymphocytes, and inactivated infectious bronchitis virus (IBV) were added as antigen to perform antigen re-stimulation assay. The proliferation of memory lymphocytes that can recognize IBV antigen of each group of chickens was compared. The methods for determining proliferation state are the same as described in Example 5. Proliferation rate=(OD of test groups/OD of RPMI 1640 culture only)×100%. Compared with the group vaccinated with IB vaccine only, the groups vaccinated with IL-2 fusion proteins as IB vaccine adjuvant (SDF1IL2+IB vaccine) ($p<0.01$) or vaccinated with $CD40L_{Exc}$ fusion proteins as IB vaccine adjuvant (SDF1CD40$L_{Exc}$+IB vaccine) ($p<0.05$) had a significantly enhanced proliferation of antigen-specific memory lymphocytes upon antigen re-stimulation (see FIG. 9).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A fusion protein, comprising:
a chemokine polypeptide, wherein the chemokine polypeptide is stromal cell-derived factor-1; and
a cytokine polypeptide connected to the chemokine polypeptide by a peptide linker,
wherein the peptide linker is a hydrophilic helical peptide linker,
wherein the cytokine polypeptide is CD40 ligand, and
wherein the fusion protein has an amino acid sequence selected from the group consisting of SEQ ID NOs: 46 and 48.

2. The fusion protein of claim 1, wherein said protein is encoded by an isolated nucleic acid molecule having the nucleotide sequence of SEQ ID NO: 45.

3. The fusion protein of claim 1, wherein said protein is encoded by an isolated nucleic acid molecule having the nucleotide sequence of SEQ ID NO: 47.

* * * * *